(12) United States Patent
Giraldo Gomez et al.

(10) Patent No.: US 11,186,845 B1
(45) Date of Patent: Nov. 30, 2021

(54) COMPOSITIONS COMPRISING A NANOPARTICLE, A MOLECULAR BASKET COMPRISING CYCLODEXTRIN, AND A CHLOROPLAST-TARGETING PEPTIDE AND METHODS OF USE THEREOF

(71) Applicant: The Regents of the University of California, Oakland, CA (US)

(72) Inventors: Juan Pablo Giraldo Gomez, Riverside, CA (US); Peiguang Hu, Riverside, CA (US); Israel Santana, Riverside, CA (US); Gregory Newkirk, Riverside, CA (US); Honghong Wu, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/218,429

(22) Filed: Dec. 12, 2018

Related U.S. Application Data

(60) Provisional application No. 62/597,843, filed on Dec. 12, 2017.

(51) Int. Cl.
| | | |
|---|---|---|
| *C12N 15/82* | (2006.01) | |
| *C12N 5/04* | (2006.01) | |
| *C12N 9/88* | (2006.01) | |
| *C07K 14/415* | (2006.01) | |

(52) U.S. Cl.
CPC ........ *C12N 15/8214* (2013.01); *C07K 14/415* (2013.01); *C12N 5/04* (2013.01); *C12N 9/88* (2013.01); *C12Y 401/01039* (2013.01)

(58) Field of Classification Search
None
See application file for complete search history.

(56) References Cited

U.S. PATENT DOCUMENTS

| | | | |
|---|---|---|---|
| 9,567,629 B2 * | 2/2017 | Nikiforov | C07H 19/20 |
| 2005/0053591 A1 * | 3/2005 | Pun | C12N 15/62 |
| | | | 424/94.1 |
| 2011/0203013 A1 * | 8/2011 | Peterson | B82Y 5/00 |
| | | | 800/279 |

FOREIGN PATENT DOCUMENTS

| | | | | |
|---|---|---|---|---|
| WO | WO-0026371 A1 * | 5/2000 | ........ | C12N 15/8214 |
| WO | 2018204439 A1 | 11/2018 | | |

OTHER PUBLICATIONS

Hu et al. Nanografting de novo proteins onto gold surfaces. (2005) Langmuir; vol. 21; pp. 9103-9109 (Year: 2005).*
Zirzow et al. Nanoscale "DNA baskets" for the delivery of siRNA. (2010) IFMBE Proceedings; Herold, Bentley, Vossoughi (Eds); Springer (Publisher); vol. 32.; pp. 130-133 (Year: 2010).*
Krings et al. Light-responsive aggregation of beta-cyclodextrin covered silica nanoparticles. (2014) Journal of Materials Chemistry A; vol. 2; pp. 9587-9593 (Year: 2014).*
Giraldo, J , et al., "Plant Nanobioengineering Team: Infrared Plant Sentinels of Chemical and Biological Threats Enable by Plastid Nanobioengineering", APT Proposers Day Poster, 1 page (2017).
Giraldo, J , "Targeted chloroplast bioengineering by nanomaterials in planta", University of California, Riverside—IIGB symposium (Invited), 27 pages (Sep. 2018).
Giraldo, J , et al., "Targeted delivery of nanomaterials with chemical cargoes in plants enabled by a biorecognition motif", Nature Communications 11, 2045, https://doi.org/10.1038/s41467-020-15731-w, 12 pages (2020).
Giraldo, J , "Targeted Foliar Delivery of Nanoparticles to Organelles for Engineering Crop Stress Tolerance", Nano 2018 (Keynote speaker), Duke University, NC, 26 pages (Sep. 2018).
Giraldo, J , "Targeted Nanoparticle Delivery to Leaf Organelles for Understanding and Engineering Plant Abiotic Stress Tolerance", Gordon Research Conference on Nano-Enabled Technologies to Improve Efficiency, Quality, and Health in Food and Agriculture (Invited), Holyoke, MA, 26 pages (Jun. 2018).
Giraldo, J , et al., "Turning Plants into Technology through Chloroplast Nanobioengineering", Stanford Bioengineering Department (Invited), Palo Alto, CA, 41 pages (Apr. 2018).
Santana, I , et al., "Targeted and Controllable Chloroplast Bioengineering by Nanomaterials in Planta", Poster, Gordon Research Conference, Ventura, CA, 8 pages (2019).

* cited by examiner

*Primary Examiner* — Cathy Kingdon Worley
(74) *Attorney, Agent, or Firm* — Viksnins Harris Padys Malen LLP

(57) ABSTRACT

Compositions for chemical and/or genetic modification of chloroplasts of plants include a functionalized nanoparticle composition linked to a chloroplast-targeting peptide and a functionalized single walled carbon nanotube (SWNT) composition complexed with a nucleic acid cassette encoding a plastid-specific ribosomal RNA operon (prrn). Methods for chemically and/or genetically modifying chloroplasts of plants include administering these chloroplast-targeted compositions to the leaves of live plants.

16 Claims, 23 Drawing Sheets
(19 of 23 Drawing Sheet(s) Filed in Color)
Specification includes a Sequence Listing.

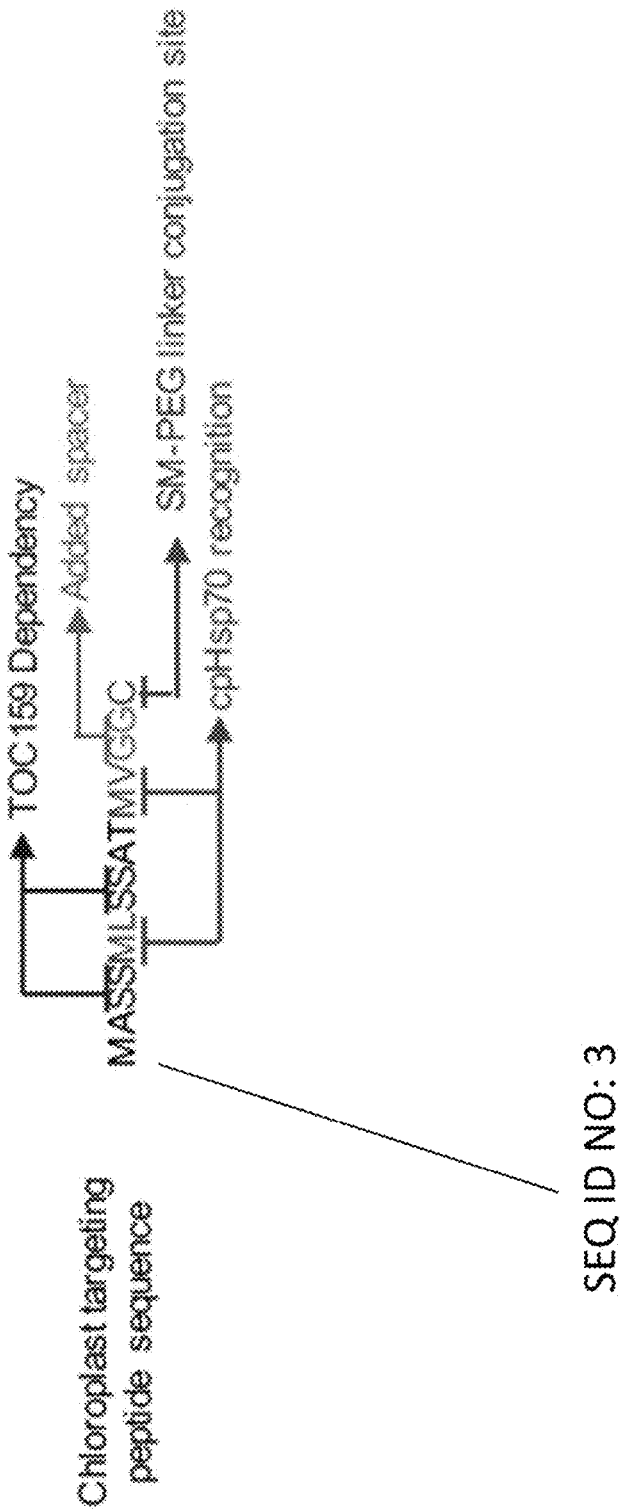

FIG. 2A

| | | | |
|---|---|---|---|
| B. Napus | 1 MASSMLSSATVV------SSPAQA-MMVAPFTGLKSS 30 | SEQ ID NO: 14 |
| B. Juncea | 1 MASSMLSSAAVV------TSPAQA-TMVAPFTGLKSS 30 | SEQ ID NO: 15 |
| B. Rapa | 1 MASSMLSSAAVV------TSPAQA-TMVAPFTGLKSS 30 | SEQ ID NO: 16 |
| P. persica | 1 MASSMISSATVASVYADRAAPAQA-SLVAPFTGLKSA 36 | SEQ ID NO: 17 |
| P. avium | 1 MASSMISSATVASVYADRAAPAQA-SLVAPFTGLKSA 36 | SEQ ID NO: 18 |
| G. Hirsutum | 1 MASSMISSATIA----TASPAQA-NMVAPFTGLKSA 31 | SEQ ID NO: 19 |
| V. Vinifera | 1 MASSMVSSATVAT--INRATPAQA-NMVAPFTGLKSL 34 | SEQ ID NO: 20 |
| R. Communis | 1 MASSMLSTATVAS----LNRASPAQA-SMVAPFTGLKST 34 | SEQ ID NO: 21 |
| C. sinensis | 1 MASSMISSTTVAT--ANRASLAQA-SMVAPFTGLKSS 34 | SEQ ID NO: 22 |
| M. Truncatula | 1 MASSMISSSAMTT--VNRASSVQS-GAVAPFVGLKSM 34 | SEQ ID NO: 23 |
| C. arietinum | 1 MASSMISSAAVTT--VNRASSVQS-GAVAPFVGLKSM 34 | SEQ ID NO: 24 |
| C. Ararbica | 1 MASSMISSAAVAT--TTRASPAQA-SMVAPFNGLKAA 34 | SEQ ID NO: 25 |
| H. Brasiliensis | 1 MASSMLSTAAVAC--INRASPAQA-SMVAPFTGLKST 34 | SEQ ID NO: 26 |
| N. attenuata | 1 MASSVLSSAAVAT------RSNVAQA-NMVAPFTGLKSA 32 | SEQ ID NO: 27 |
| S. tuberosum | 1 MASSVISSAAVAT------RTNVTQASSMVAPFTGLKST 33 | SEQ ID NO: 28 |
| S. lycopersicum | 1 MASSVISSAAVAT------RSNVTQA-SMVAPFTGLKSS 32 | SEQ ID NO: 29 |
| P. Vulgaris | 1 MASSMISSPAVTT--VRAG-AGA-GMVAPFTGLKSL 33 | SEQ ID NO: 30 |
| G. max | 1 MASSMISSPAVTT--VRAG-----A-GMVAPFTGLKSM 31 | SEQ ID NO: 31 |
| C. Annuum | 1 MASSVMSIAPVAT----GANAAQA-SMIASFNGLKSA 32 | SEQ ID NO: 32 |
| V. Radiata | 1 MASSMISSPAVTT--VRAG-A-A-GMVAPFTGLKSL 32 | SEQ ID NO: 33 |
| M. Acuminata | 1 MASSMMVSSAAT------VSRASPAQS-SMVAPFTGLKST 33 | SEQ ID NO: 34 |
| A. Hypogaea | 1 MAISMISSPAVTT--VSRASPAQA-NMVAPFTGLKSL 34 | SEQ ID NO: 35 |
| A. thaliana | 1 MASSMLSSATMV------ASPAQA-TMVAPFNGLKSS 30 | SEQ ID NO: 36 |

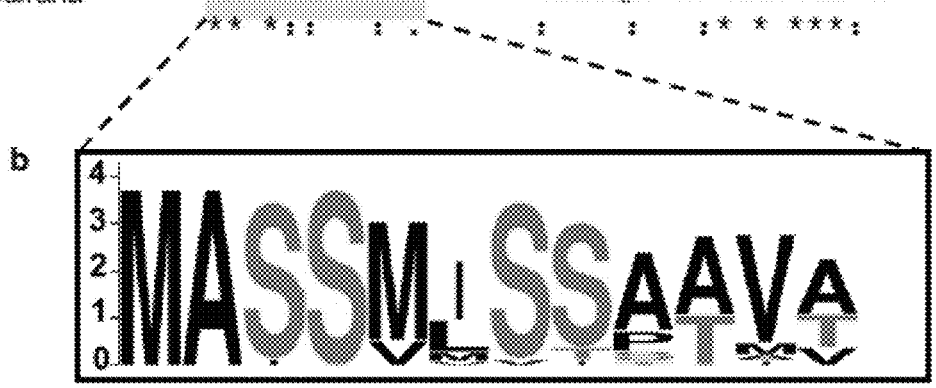

FIG. 4

| Molecules | Function | Reference |
|---|---|---|
| Allyl isothiocyanate | Antimicrobial | Li et al 2007 |
| Chlorpyrifos | Insecticide | Lucas-Abellán et al 2008 |
| Hesperetin, hesperidin, naringenin and naringin | Flavonoids | Ficarra et al 2002 |
| 2-methyl-5-(1-methylethyl) (carvacrol) | Reduce intestinal parasitic infection | Shashank et al 2018 |
| Nicotinic acid and ascorbic acid | Vitamins and antioxidants | Subhadeep et al 2016, Garnero et al 2007, Palomar-Pardavé et al 2011 |
| Methyl viologen | Herbicide | Sivagnanam et al 1992, Ong et al 2003, Mondal et al 2016 |
| Dihydroxyphenylalanine (L-DOPA) | Neurotrophic factor | Palomar-Pardavé et al 2011 |
| Theophylline | Alkaloid treatment of respiratory diseases | Behera 2015 |
| Amatadine | Antiviral agent | Ai et al 2012 |
| beta-Carotene | Vitamin | Kaur et al 2016 |
| Nitrophenol isomers | Precursor pharmaceutical and chemical production | Zhang et al 2015 |
| Alkaline phosphatase | Clinical disease indicator | Jia et al 2010 |
| Napthalene | Insecticide | Harata et al 1975 |
| Terfenadine | antihistamine | Choi et al 2001 |
| Carvedilol | antioxidant | Wen et al 2004 |
| Sulindac, Fenoprofen | Non estradiol anti-inflammatory | Llarduya et al 1998, Diaz et al 1999 |
| Albendazole | intestinal parasite treatment | Garcia et al 2014 |
| Cocaine | Stimulant | Nesnas et al 2000 |

FIG. 6C
SEQ ID NO: 37

COMPOSITIONS COMPRISING A NANOPARTICLE, A MOLECULAR BASKET COMPRISING CYCLODEXTRIN, AND A CHLOROPLAST-TARGETING PEPTIDE AND METHODS OF USE THEREOF

CROSS-REFERENCE TO RELATED APPLICATION

The present application claims priority to and the benefit of U.S. Provisional Application Ser. No. 62/597,843 filed on Dec. 12, 2017, entitled "PLANT CHLOROPLAST AND MITOCHONDRIA GENETIC ENGINEERING ENABLED BY FOLIAR SPRAYED NANOPARTICLES," the entire content of which is incorporated herein by reference.

STATEMENT REGARDING FEDERALLY SPONSORED RESEARCH OR DEVELOPMENT

This invention was made with government support under Grant No. 1817363 awarded by the National Science Foundation. The government has certain rights in the invention.

INCORPORATION BY REFERENCE

The instant application contains a Sequence Listing which has been submitted in ASCII format via EFS-Web and is hereby incorporated by reference in its entirety. Said ASCII copy was created on Mar. 14, 2019, is named 163895SEQ-LISTING.txt, and is 13,663 bytes in size.

BACKGROUND

Chloroplasts are photosynthetic, semi-autonomous organelles that are essential for fixing carbon in plants. In addition, chloroplasts act as signaling organelles and play key roles in the synthesis of metabolites. These photosynthetic plastids, which have a prokaryotic-like genome, are excellent targets for genetic engineering tools due to the ability to isolate genetic markers in parental lines, minimize outcrossing of transgenes to other crops, multiple genes encoded in one plasmid, and the lack of silencing mechanisms. However, conventional chloroplast transformation techniques are limited to less than 10 plant species due to the absence of a chloroplast-specific delivery mechanism.

SUMMARY

Aspects of embodiments of the present disclosure are directed to nanocompositions for the chemical and/or genetic modification of chloroplasts in plants.

In some embodiments of the present disclosure, a composition includes a nanoparticle linked to a chloroplast-targeting peptide where the nanoparticle is linked to the chloroplast-targeting peptide with a conjugation linker having a first end moiety conjugated to the nanoparticle and the second end moiety conjugated to the chloroplast targeting peptide.

In some embodiments of the present disclosure, the first end moiety and the second end moiety of the conjugation linker are independently selected from a functional group having a carboxyl, an amine, a thiol, a maleimide, a hydroxyl, a hydrazide, an azide, a biotin, or a succinimidyl ester (NHS ester)

In some embodiments of the present disclosure, the conjugation linker also includes cyclodextrin.

In some embodiments of the present disclosure, the nanoparticle composition also includes a molecule that forms an inclusion complex with the cyclodextrin. Examples of a molecule that forms an inclusion complex with cyclodextrin include allyl isothiocyanate, chlorpyrifos, hesperetin, hesperidin, naringenin, naringin, 2-methyl-5-(1-methylethyl) (carvacrol), nicotinic acid, ascorbic acid, methyl viologen, dihydroxyphenylalanine (L-DOPA), theophylline, amatadine, beta-carotene, nitrophenol isomers, alkaline phosphatase, naphthalene, terfenadine, carvedilol, sulindac, fenoprofen, albendazole, or cocaine.

In some embodiments of the present disclosure, the chloroplast-targeting peptide linked to the nanoparticle composition is the chloroplast targeting sequence of the ribulose bisphosphate carboxylase small chain 1A (RBCS1A) protein. In some embodiments, a three amino acid spacer of X1-X2-Cysteine (C) is added to the end of the chloroplast-targeting sequence, wherein X1 and X2 are each any amino acid except cysteine or methionine and the cysteine (C) is conjugated to the second end moiety. In some embodiments, X1 and X2 are each independently selected from glycine or histidine. In some embodiments, the chloroplast-targeting sequence has an amino acid sequence of SEQ ID NO: 1.

In some embodiments of the present disclosure, the conjugation linker of the nanoparticle composition has a first end moiety including a mercaptocarboxylic acid selected from mercaptoacetic acid, mercaptopropionic acid, mercaptosuccinic acid, mercaptobenzoic acid, mercaptoundecanoic acid, and combinations thereof.

In some embodiments of the present disclosure, the conjugation linker of the nanoparticle composition has a second end moiety including sulfosuccinimidyl 4-[N-maleimidomethyl] cyclohexane-1-carboxylate (Sulfo-SMCC), succinimidyk[N-maleimidopropionamido]-n-ethyleneglycol) ester (SM(PEG)n) with n=2, 4, 6, 8, 12, 24, and/or 1-Ethyl-3-[3-dimethylaminopropyl]carbodiimide hydrochloride-N hydroxysulfosuccinimide (EDC-Sulfo-NHS).

In some embodiments of the present disclosure, the nanoparticle is a quantum dot wherein the nanoparticle is a quantum dot having a core including carbon, nitrogen, oxygen, or any combination of carbon, nitrogen, and oxygen, or the quantum dot has a core including cadmium telluride (CdTe), cadmium selenide (CdSe), $CdSe_xTe_{1-x}$, cadmium sulfide (CdS), indium arsenide (InAs), indium lead (InPb), cadmium lead sulfide (plumbanethione-cadmium) (CdPbS), zinc tin sulfide (ZnSnS), zinc sulfide (ZnS), lead sulfide (PbS), or lead selenide (PbSe), lead telluride (PbTe), mercury sulfide (HgS), mercury selenide (HgSe), mercury telluride (HgTe), cadmium mercury telluride (CdHgTe), gallium arsenide (GaAs), or an alloy thereof.

In some embodiments of the present disclosure, a composition of a functionalized single walled nanotube (SWNT) composition complexed with a nucleic acid cassette (e.g., DNA cassette) includes a plastid-specific ribosomal RNA operon (prrn).

In some embodiments of the present disclosure, the SWNT is coated with polyethylenimine (PEI) and/or ethylenediamine (EDA) molecules and the nucleic acid cassette complexes with the PEI molecules.

In some embodiments of the present disclosure, the nucleic acid cassette complexed with the SWNT encodes for an RNA molecule or a target protein to be expressed in a chloroplast of a plant.

In some embodiments of the present disclosure, the nucleic acid cassette complexed with the SWNT encodes a 5' untranslated region for mRNA stability.

In some embodiments of the present disclosure, a method for transporting a biomolecule or chemical to a chloroplast of a plant includes administering the nanoparticle composition linked to a chloroplast-targeting peptide as disclosed herein.

In some embodiments of the present disclosure, a method of introducing a recombinant gene to a plastid of a plant includes administering the single walled carbon nanotubes complexed with a nucleic acid cassette encoding a plastid-specific ribosomal RNA operon.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, together with the specification, illustrate example embodiments of the present disclosure, and, together with the description, serve to explain principles of the present disclosure.

FIG. 1C is a schematic of the chloroplast targeting peptide sequences of the Rubisco small subunit protein (RBSC1) for translocation across chloroplast membranes including the recognition sites for chloroplast import machinery (translocon/TOC), a cysteine residue at the C-terminus for conjugation site a SM-PEG linker, and two glycine (G) amino acids for spacers and for increasing the peptide solubility, according to embodiments of the present disclosure.

FIG. 2A is a multiple sequence alignment analysis (Cluster Omega) of Rubisco small subunit 1A chloroplast transit peptide sequences in common dicot crops and *Arabidopsis thaliana*. "*" indicates the identical amino acids among all the aligned sequences. ":" and "." indicate conserved substitutions in which an amino acid is replaced by another one with similar properties, and an empty space represents a non-conserved substitution, dash lines are introduced for optimal alignment and maximum similarity between all compared sequences, with a frequency logo plot of Rubisco subunit 1A in which a score of 4 on the y-axis means 100% conservation, according to embodiments of the present disclosure.

FIG. 4 is table of chemicals forming inclusion complexes with beta-cyclodextrin, according to embodiments of the present disclosure.

FIG. 6C is a nucleotide sequence map of amplified GFP gene cassette bound to SWCNT (GFP-SWCNT) showing annotations, according to embodiments of the present disclosure.

DETAILED DESCRIPTION

Figure 1A:
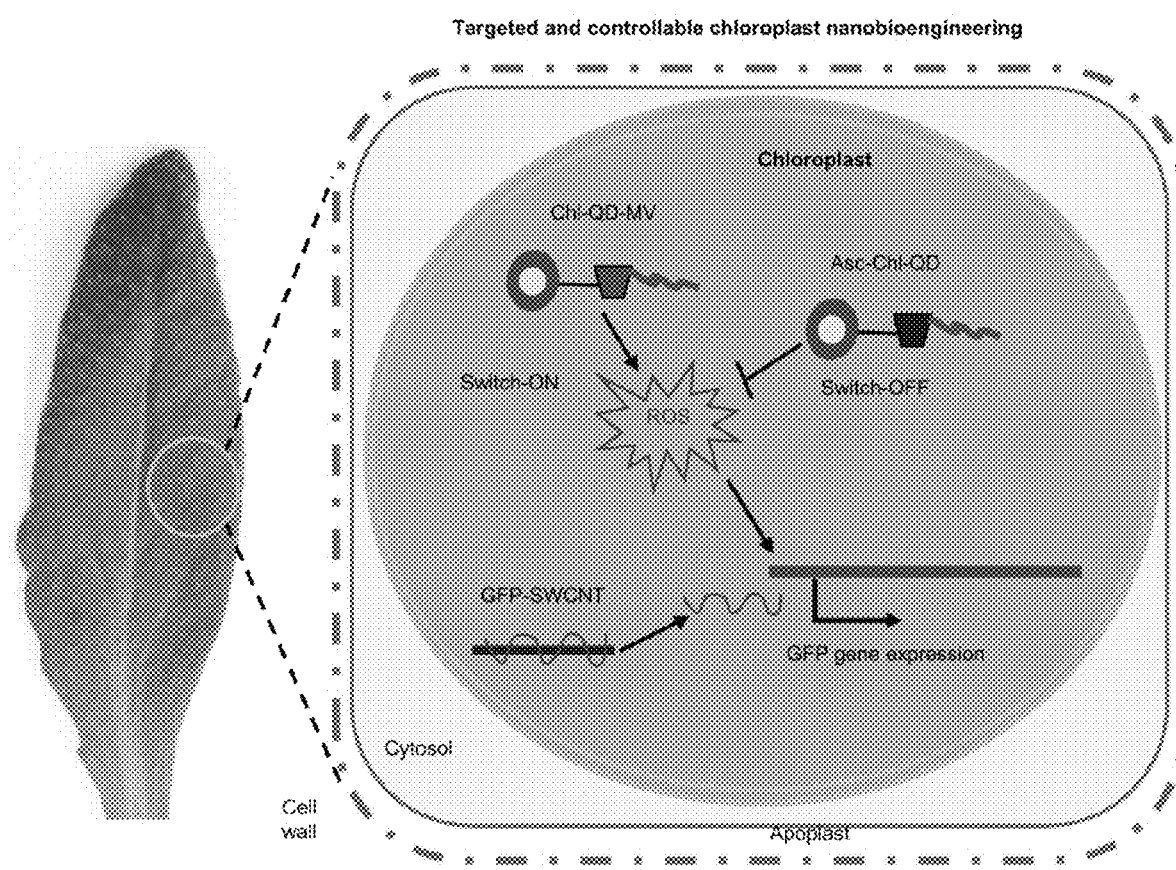
FIG. 1A is a schematic diagram representing nanocompositions for the modification and genetic transformation of plant chloroplasts, according to embodiments of the present disclosure. The depicted nanocompositions include nanoparticles (e.g., quantum dots (QD)) and single walled carbon nanotubes (SWNT). The QDs having a yellow core and red coating are functionalized with chloroplast targeting peptides and a beta-cyclodextrin (β-CD) molecular basket loaded with methyl viologen (MV-Chl-QD) or ascorbic acid (Asc-Chl-QD) to modify the redox state of chloroplasts and the SWNT have chloroplast-specific transcriptional regulation sequences in a green fluorescent protein (GFP) reporter gene cassette where upon delivery of the GFP gene cassette a single walled carbon nanotube (SWNT) can be induced to express GFP in the chloroplast of plants, according to embodiments of the present disclosure.

Although *Arabidopsis thaliana* is a model plant species that is widely used in plant sciences, to date no tools or techniques allow for the transformation of *Arabidopsis* chloroplasts, thereby impeding the research of chloroplast biology and bioengineering.

Aspects of embodiments of the present disclosure include engineered nanocompositions for biochemical delivery to or genetic transformation of a chloroplast in a plant cell. In some embodiments of the present disclosure, these engineered nanocompositions include a quantum dot (QD) composition capable of being transported into a chloroplast and a single walled carbon nanotube (SWNT) capable of passively entering a plant cell.

In some embodiments of the present disclosure, a cargo-loaded quantum dot is functionalized with a chloroplast-specific transit peptide that is capable of transporting the functionalized quantum dot across the membrane of the chloroplast for delivery of the molecular or chemical cargo load into the chloroplast. In some embodiments of the present disclosure, using a nucleic acid expression cassette having a plastid-specific operon, a single walled carbon nanotube (SWNT or SWCNT) complexed with the nucleic acid expression cassette is capable of passively enter a plant cell in which expression of the recombinant protein encoded by the nucleic acid cassette only occurs in a plastid (e.g., a chloroplast) of the plant cell.

As used herein, the terms "quantum dot" and "QD" refer to a nanoscale particle having a core material and a coating material covering the core. The quantum dot may also be referred to herein as a nanoparticle. The nanoscale particle (e.g., quantum dot) as disclosed herein may have a diameter in a range of about 1 nanometers (nm) up to about 100 nm. The diameter may be within any range that can be defined by the foregoing values. For example, the diameter (e.g., a $D_{50}$ average diameter) may be in a range of about 1 to about 20 nm (e.g., for spherical or disc-shaped nanoparticles such as, for example, quantum dots). The nanoparticle may have a diameter of about 1 to about 20 nm. In some embodiments, the nanoparticle has a diameter of about 2 nm to about 8 nm. For example, the nanoparticle may have a diameter of about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, or about 30 nm. The nanoparticle may also have a diameter of about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, or about 100 nm.

In some embodiments of the present disclosure, the nanoparticle (e.g., quantum dot) has a core material selected from cadmium telluride (CdTe), cadmium selenide (CdSe), $CdSe_xTe_{1-x}$, cadmium sulfide (CdS), indium arsenide (InAs), indium lead (InPb), cadmium lead sulfide (plumbanethione-cadmium) (CdPbS), zinc tin sulfide (ZnSnS), zinc sulfide (ZnS), lead sulfide (PbS), or lead selenide (PbSe), lead telluride (PbTe), mercury sulfide (HgS), mercury selenide (HgSe), mercury telluride (HgTe), cadmium mercury telluride (CdHgTe), gallium arsenide (GaAs), or an alloy thereof.

In some embodiments of the present disclosure, the nanoparticle includes (e.g., may be made of at least) a semiconductor, metal, and/or metal oxide (e.g., gold, silver, copper, titanium, nickel, platinum, palladium, oxides thereof (e.g., $Cr_2O_3$, $CO_3O_4$, NiO, MnO, $CoFe_2O_4$, and $MnFeO_4$), and alloys thereof), metalloid and metalloid oxide nanoparticles, the lanthanide series metal nanoparticles, and combinations thereof. Semiconductor quantum dots are described in U.S. Pat. No. 6,468,808 and International Patent Application WO 03/003015, the entire contents of both of which are incorporated herein by reference.

In some embodiments, the nanoparticle also includes a quantum dot having a core of carbon, nitrogen and/or oxygen or a silicon quantum dot having a core including silicon.

In some embodiments, the quantum dots includes a core and a coating (e.g., a shell), however, uncoated quantum dots may be used as well. In some embodiments, if a shell is covering the core, the shell material may passivate the core by having a higher band gap than the core. For example, if the core is CdTe or CdSe, the shell may be CdS, and if the core is CdS (or CdSe or CdTe), the shell may be ZnS.

In some embodiments of the present disclosure, the nanoparticle may have a covering surrounding the core material. For example, the nanoparticle (e.g., quantum dot) may have a covering material (e.g., a shell or shell material) including cadmium sulfide (CdS). In some embodiments, however, uncoated quantum dots may be used as well. In some embodiments, if a shell is covering the core, the shell material may passivate the core by having a higher band gap than the core. For example, if the core is CdTe or CdSe, the shell may be CdS, and if the core is CdS (or CdSe or CdTe), the shell may be ZnS.

As used herein, the term "conjugation linker" refers to a molecule or compound to facilitate binding of the quantum dot to a peptide. In some embodiments, the peptide is a chloroplast-specific transport peptide. A conjugation linker has one end that binds the first molecule (e.g., the quantum dot) and a second end that binds the second molecule (e.g., the peptide). The conjugation linker has a first end and a second end, however, the conjugation linker may vary in length. For example, in some embodiments of the present disclosure, the conjugation linker may also include cyclodextrin. The presence of cyclodextrin in the conjugation linker allows for the loading of molecules that form inclusion complexes with cyclodextrin. Examples of conjugation linkers are provided herein, but the present disclosure is not limited thereto. Upon reviewing the present disclosure, a person of ordinary skill in the art should readily be able to determine the appropriate conjugation linker depending on the type of coating on the quantum dot.

The terms "functionalized quantum dot" and "functionalized nanoparticle" as disclosed herein and according to embodiments of the present disclosure, refer to a a nanoparticle or quantum dot as defined herein having a conjugation linker having a first end linked to the outermost surface (e.g., core or shell) of the nanoparticle or the quantum dot and a second end linked to a peptide (e.g., a chloroplast-transport peptide).

As used herein, the term "single walled carbon nanotube" may be abbreviated as SWNT or SWCNT. The single walled carbon nanotubes of the present disclosure have a cylindrical shape with a diameter from about 1 nm up to about 20 nm. In some examples, the SWNT has a diameter of less than 1 nm. In some embodiments, the SWNT has a diameter in a range of about 1 nm to about 15 nm, about 1 nm to about 10 nm, about 5 nm to about 20 nm, about 5 to about 15 nm, about 10 to about 20, or about 10 nm to about 15 nm. In some embodiments, the SWNT has a length on the order of microns, tens of microns, hundreds of microns, or millimeters. In some embodiments, the SWNT has a length up to about 900 nm.

As used herein, the term "any amino acid" refers to any biocompatible amino acid that is capable of forming a peptide bond. Abbreviations for amino acids may be used throughout this disclosure and follow the standard nomenclature used in the art. For example, as would readily be understood by those or ordinary skill in the art, amino acids include and may be abbreviated as follows: Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Theonine is Thr or T; Tryptophan is Trp or W; Tyrosine is Tyr or Y; and Valine is Val or V.

As used herein nucleic acids include deoxyribose nucleic acid (DNA) and ribonucleic acid (RNA), where cDNA refers to copy DNA and mRNA refers to messenger RNA.

As used herein, the term "about" in relation to a given numerical value is meant to include numerical values within 10% of the specified value.

With reference to FIG. 1A, two quantum dots having a yellow core and red coating are schematically shown in the chloroplast of a plant cell in which each of the two quantum dots is conjugated to a chloroplast-peptide (Chl) with a conjugation linker including cyclodextrin (represented as a bucket/basket) with methyl viologen (MV) complexed with cyclodextrin in one of the quantum dots as indicated, and ascorbic acid (Asc) is complexed with cyclodextrin in the other quantum dot as indicated.

In some embodiments of the present disclosure, the conjugation linker has a first end moiety that includes a thiol group and/or a carboxylic acid group. For example, a first end moiety including a thiol group and/or a carboxylic acid group includes a mercaptocarboxylic acid. In some embodiments, the first end moiety of the conjugation linker is a mercaptocarboxylic acid selected from mercaptoacetic acid, mercaptopropionic acid, mercaptosuccinic acid, mercaptobenzoic acid, mercaptoundecanoic acid, and combinations thereof.

Figure 1B:
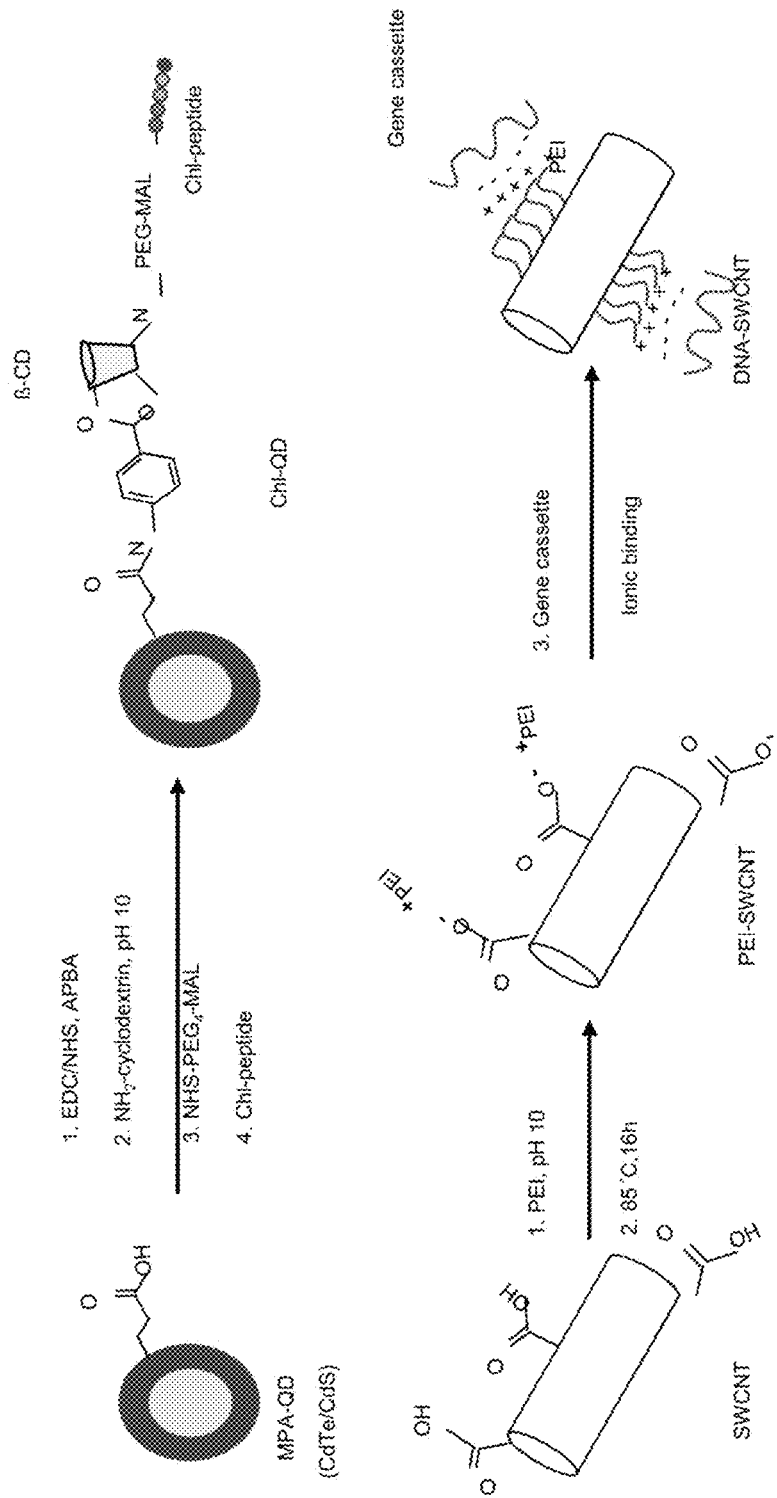
FIG. 1B is a schematic of example synthesis reactions of the chloroplast-targeted quantum dot (Chl-QD) and single walled carbon nanotube-DNA (DNA-SWNT) platforms for biomolecule and gene delivery to chloroplasts, according to embodiments of the present disclosure.

With reference to FIG. 1B, an example reaction scheme is shown wherein mercaptopropionic acid (MPA) is conjugated to the coating of the CdTe/CdS quantum dot. With reference to both FIGS. 1A-1B, the conjugation linker may also include cyclodextrin. Examples of cyclodextrin include alpha-, beta-, and gamma-cyclodextrin. In some embodiments, the conjugation linker includes beta-cyclodextrin which binds to a wide range of amphiphilic and hydrophobic molecules. Accordingly, using a functionalized quantum dot having a chloroplast-specific transport peptide together with a conjugation linker including beta-cyclodextrin allows for the loading of biomolecules that form inclusion complexes with beta-cyclodextrin onto the quantum dot for transport of the complexed molecule to the plant chloroplast. Non-limiting examples of biomolecules that form inclusion complexes with beta-cyclodextrin are listed in the table of FIG. 4, and include allyl isothiocyanate, chlorpyrifos, hesperetin, hesperidin, naringenin, naringin, 2-methyl-5-(1-methylethyl) (carvacrol), nicotinic acid, ascorbic acid, methyl viologen, dihydroxyphenylalanine (L-DOPA), theophylline, amatadine, beta-carotene, nitrophenol isomers, alkaline phosphatase, naphthalene, terfenadine, carvedilol, sulindac, fenoprofen, albendazole, and cocaine. Each of these biomolecules forming inclusion complexes with beta-cyclodextrin are described in the corresponding reference as indicated in FIG. 4. These references include Ai et al., Talanta 99, 409-414 (2012); Ammar et al., Theophylline Pharmazie 51, 42-46 (1996); Choi et al., Drug Dev. Ind. Pharm. 27, 857-862 (2001); Diaz et al., Drug Dev. Ind. Pharm. 25, 107-110 (1999); Ficarra et al., J. Pharm. Biomed. Anal. 29, 1005-1014 (2002); Garcia et al., PLoS One 9, e113296 (2014); Garnero et al., J. Pharm. Biomed. Anal. 45, 536-545 (2007); Harata et al., BCSJ 48, 375-378 (1975); Kaur et al., Plan. Perspect. 5, 2016; Nesna et al., Bioorg. Med. Chem. Lett. 10, 1931-1933 (2000); Jia et al., Chem. Commun. 46, 7166-7168 (2010); Lucas-Abellán et al., J. Agric. Food Chem. 56, 8081-8085 (2008); Li et al., Food Chem. 103, 461-466 (2007); Mondal et al., J. Phys. Chem. C 120, 14365-14371 (2016); Ong et al., J. Org. Chem. 69, 1383-1385 (2004); de Oliveira et al., J. Phys. Chem. A 115, 8511-8519 (2011); Palomar-Pardavé et al., J. Incl. Phenom. Macrocycl. Chem. 69, 91-99 (2011); Sivagnanam et al., J. Electroanal. Chem. 341, 197-207 (1992); Tros de Ilarduya et al., Drug Dev. Ind. Pharm. 24, 301-306 (1998); Wen et al., J. Pharm. Biomed. Anal. 34, 517-523 (2004); and Zhang et al., Nanoscale 7, 19540-19546 (2015), the entire contents of all of these references are incorporated herein by reference.

With continued reference to FIG. 1A, each of the two quantum dots schematically shown in the chloroplast of a plant cell is conjugated to a chloroplast-peptide (Chl) with a conjugation linker that includes cyclodextrin with methyl viologen (MV) complexed with cyclodextrin in one of the quantum dots as indicated, and ascorbic acid (Asc) is complexed with cyclodextrin in the other quantum dot as indicated. According to embodiments of the present disclosure, methods for upregulating (indicated as "switch-ON") the level of reactive oxygen species (ROS) (e.g., free radicals) in the chloroplast of a plant cell include the use of a quantum dot conjugated to a chloroplast transport peptide along with cyclodextrin complexed with methyl viologen (MV) to transport the MV into the chloroplast. In some embodiments, methods for downregulating (indicated as "switch-OFF") the level of ROS in the chloroplast of a plant cell include the use of a quantum dot conjugated to a chloroplast transit peptide along with cyclodextrin complexed with ascorbic acid (Asc) to transport the Asc into the chloroplast. Accordingly, the delivery of MV and Asc by QDs allows for tunable changes in chloroplast redox states by inducing or reducing superoxide production (ROS) in plant cell chloroplasts. Furthermore, regulating the oxidative status in chloroplasts allows for control of redox-sensitive gene expression.

In some embodiments of the present disclosure, the peptide conjugated to the quantum dot is a chloroplast-transport peptide. Examples of a chloroplast-transport peptide include the 12 amino acid chloroplast targeting sequence (MASSMLSSATMV)(SEQ ID NO: 1) of the *Arabidopsis thaliana* ribulose bisphosphate carboxylase small chain 1A (RBCS1A, genbank: OAP15425) protein as shown schematically in FIG. 1C. The sequence shown in FIG. 1C (SEQ ID NO: 3) also includes a three amino acid spacer of glycine-glycine-cysteine (G-G-C). With reference to FIG. 2A, the *Arabidopsis thaliana* chloroplast targeting sequence (the 12 amino acids bracketed with a blue line) is highly conserved among at least the dicot plants listed in FIG. 2A. Accordingly, chloroplast-specific targeting and transport may be carried out in a variety of dicotyledon plants (e.g., dicot plants) using the corresponding RBCS1A targeting sequence.

In some embodiments of the present disclosure, a three amino acid spacer is added to the 12 amino acid targeting sequence. Examples of the three amino acid spacer include X1-X2-C, wherein each of X1 and X2 are any amino acid and the terminal cysteine (C) is conjugated to the second end moiety. In some embodiments, each of X1 and X2 are independently selected from glycine (G), histidine (H), and combinations thereof.

In some embodiments of the present disclosure, the second end of the conjugation linker is a moiety capable of conjugating the peptide. For example, with reference to FIG. 1C, for conjugation to the C-terminal cysteine (C) of the G-G-C spacer added to the chloroplast targeting sequence, a thiol bond may be formed between the cysteine and a maleimide second end group (e.g., SM-PEG) of the conjugation linker. Examples of maleimide-containing molecules include sulfosuccinimidyl 4-[N-maleimidomethyl] cyclohexane-1-carboxylate (Sulfo-SMCC), succinimidyk[N-maleimidopropionamido]-n-ethyleneglycol) ester (SM(PEG)n) with n=2, 4, 6, 8, 12, 24, and/or 1-Ethyl-3-[3-dimethylaminopropyl]carbodiimide hydrochloride-N hydroxysulfosuccinimide (EDC-Sulfo-NHS).

In some embodiments of the present disclosure, the first and second end moieties (e.g., functional groups) of the conjugation linker may include any suitable functional group or groups for covalently or non-covalently bonding the nanoparticle to the chloroplast-targeting peptide. Non-limiting examples of functional groups for the first and/or second end moiety of the conjugation linker include a carboxyl, an amine, a thiol, a maleimide, a hydroxyl, a hydrazide, an azide, a biotin, or a succinimidyl ester (NHS ester). Methods for conjugating a functional group or groups to the surface (e.g., core or shell) of the nanoparticle and to chloroplast-targeting peptide are known in the art and as described in *Bioconjugate Techniques*, Third Edition, Greg T. Hermanson, Pierce Biotechnology, Thermo Fisher Scientific, Rockford, Ill., Academic Press, ISBN-13: 978-0123822390, the entire content of which is incorporate herein by reference.

Using a dicot chloroplast transport peptide (e.g., a RBCS1A chloroplast targeting peptide sequence), molecular cargo may be provided to leaves of living dicot plants and thereby transported into the chloroplasts of the plants. For administration of (e.g., delivery of) the functionalized quantum dots according to embodiments of the present disclosure, a suspension of the functionalized quantum dots may be provided to the leaf of an intact living plant. Examples of administering the quantum dots to the leaves of living plants are described herein, but the present disclosure is not limited thereto.

With reference to FIG. 1B, single-walled carbon nanotubes (SWNT) coated with (e.g., ionically complexed with) nucleic acids scaffolds (e.g., DNA) can passively enter plant cells. In some embodiments of the present disclosure, the nucleic acids include a gene expression cassette having plastid-specific expression sequences for chloroplast-only expression of a desired RNA molecule or a recombinant protein.

Figure 6A:
FIG. 6A is a plasmid sequence map of synthesized GFP cassette (pUCIDT-KAN g10-AtGFP.gb), according to embodiments of the present disclosure.

For complexing of negatively charged nucleic acids (e.g., DNA) the SWNT is coated with a positively charged molecule. For example, with reference to FIG. 1B, the SWNT may be coated with the positively charged amine molecules e.g. polyethyleneimine (PEI) and/or ethylenediamine (EDA). With reference to FIG. 6A, a SWNT coated with PEI is complexed with a DNA cassette encoding a green fluorescent protein (GFP) reporter protein having a plastid ribosomal RNA operon (prrn) specifically transcribed by the chloroplast expression machinery as described in Suzuki et al., 2003, *Plant Cell*, 15:195-205, the entire content of which is incorporated herein by reference. In some embodiments of the present disclosure, the expression cassette also includes additional sequences for expression fidelity. For example, the GFP expression cassette used herein (e.g., as used in FIG. 6A) also encodes a T7g10 5' untranslated region to confer improved mRNA stability, as described in Svab et al., 1990, *PNAS*, 87:8526-8530, the entire content of which is incorporated herein by reference.

The following examples are presented for illustrative purposes only, and do not limit the scope or content of the present application.

EXAMPLES

Example 1. Preparation of p-Aminophenylboronic acid capped QDs (APBA/QDs)

The MPA-QDs terminal Carboxyl group was functionalized by 1-Ethyl-3-(3-dimethylaminopropyl)carbodiimide (EDC) and N-hydroxysuccinimide (NHS) activated reaction. Briefly, NHS (2×10−6 mol) and EDC/HCl (2×10−6 mol) were added to the 1 nmol of the MPA-capped QDs in TES buffer (10 mM TES buffer, pH 7.4), the mixture was gently stirred for 15 minutes at room temperature. Next 80 µl of a 0.025 M APBA solution was added to the activated MPA-QD solution to generate aminophenyl boronic acid functionalized quantum dots (BA-QD). The reaction was stirred for 3 hours at room temperature. Finally, the excess of APBA was removed by washing twice through a 10K Amicon® filter with double distilled water (ddH$_2$O). The BA-QDs solution were sonicated for 15 min at 80% power at 37 hz to break down any agglomerated particles.

Example 2. Preparation of β-CD-Capped QDs

The resulting BA-QDs were dissolved in 10 mM TES buffer pH 10.4. Then 1 µmol of β-cyclodextrin (β-CD) in water was added to the BA-QD solution and allowed to react overnight at room temperature with gentle stirring. The excess of β-cyclodextrin was removed by washing with a 10k Amicon® filter followed by sonication for 30 minutes at 80% power at 37 hz. The resulting β-Cyclodextrin coated quantum Dots (β-CD-QD) were suspended in 10 mM TES pH 7.4.

Example 3. Peptide-Conjugated β-CD-Capped QDs

Figure 2B:
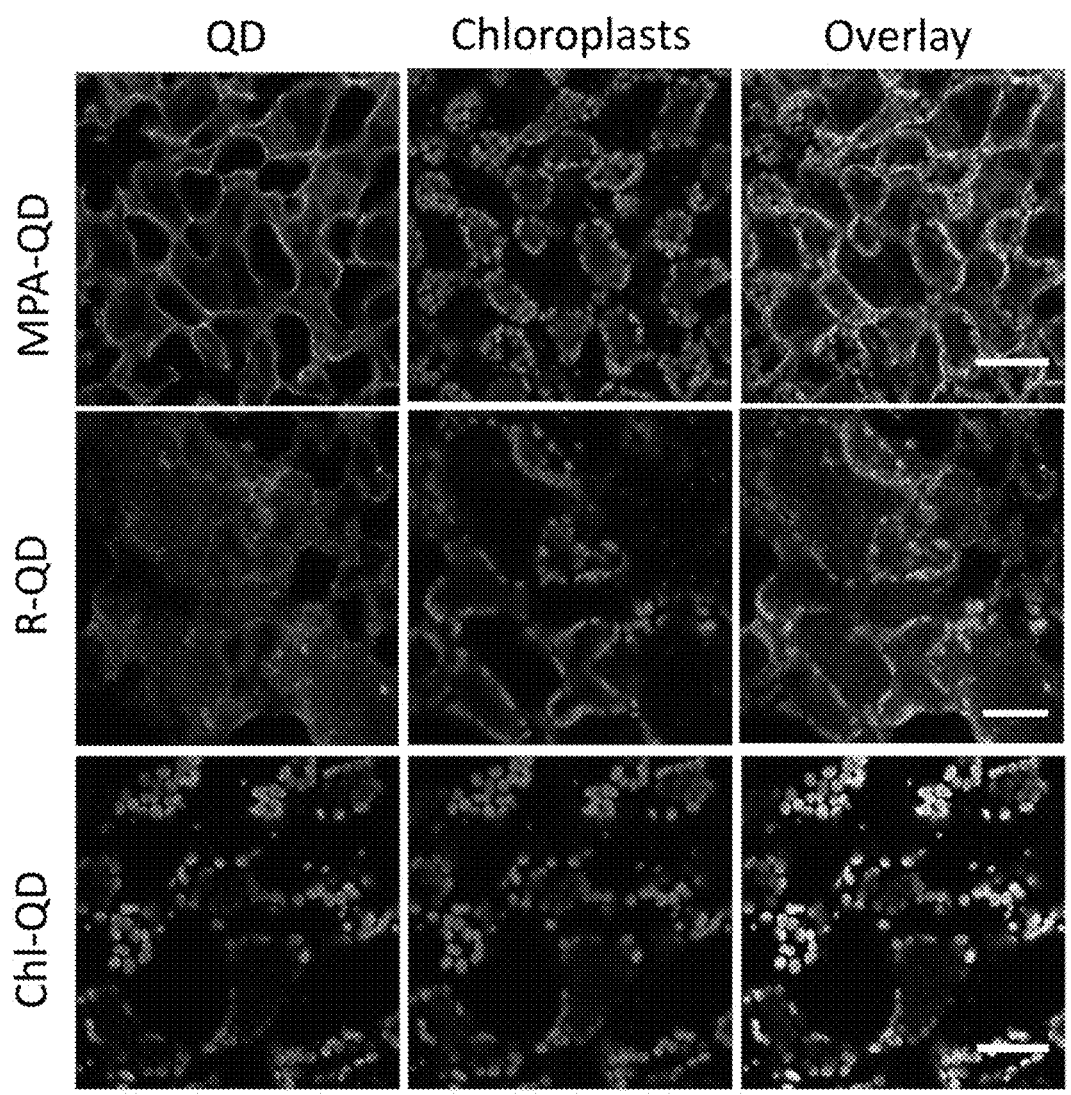
FIG. 2B shows a panel of confocal images showing localization of Chl-QDs with chloroplasts in leaf mesophyll cells compared to QDs without targeting peptide (MPA-QDs) and QDs coated with a randomized amino acid sequence of Rubisco small subunit 1A peptide (R-QDs), according to embodiments of the present disclosure, in which the scale bar is 40 μM.
Figure 2C:
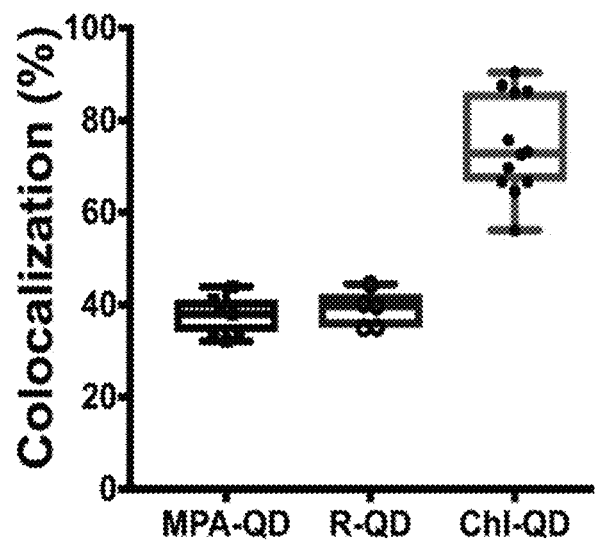
FIG. 2C is a graph of the colocalization analysis of Chl-QD, MPA-QD and R-QD with chloroplasts, as indicated, according to embodiments of the present disclosure.
Figure 2D:
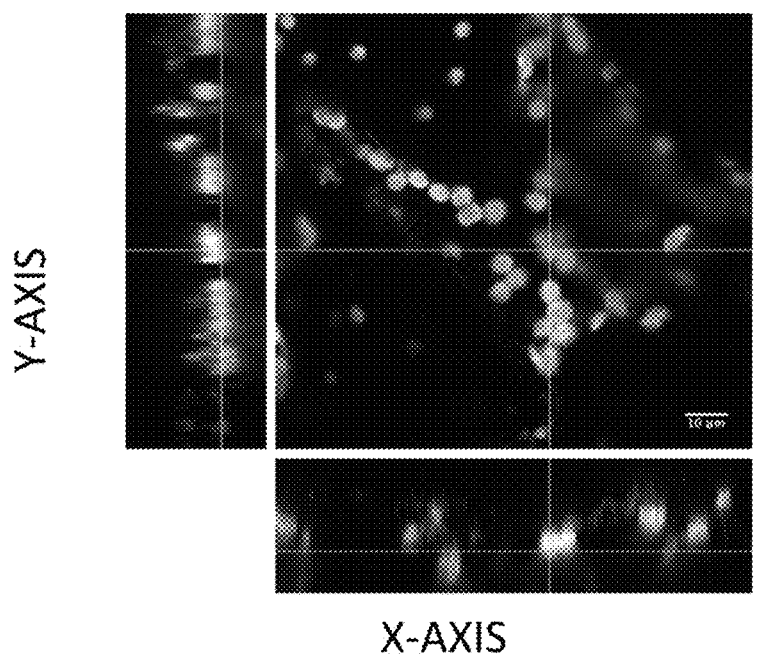
FIG. 2D shows orthogonal views of different confocal image planes showing Chl-QD colocalization within the chloroplast envelopes, according to embodiments of the present disclosure, with a scale bar of 10 μM.

1 µmol SM-PEG linker (4-maleimidobutyric acid N-succinimidyl ester linker, PHB 944) was added to the resulting 13-CD-QD containing a terminal amine to form a covalent bond. The mixture was incubated at room temperature for 1 hour (h) with gentle shaking. The excess SM-PEG was removed by washing through a 10K Am icon column with ddH$_2$O and the product was suspended in 10 mM TES pH 7.5. Finally, 1 µmol of chloroplast targeting peptide sequence from rubisco small subunit 1A (RBCS) was dissolved in the minimum volume of DMSO and was diluted with TES buffer having a pH of 8.5. The RBCS peptide was added to SM-PEG-QD and allowed to react for 1 h at room temperature with gentle shaking. The resulting chloroplast targeting quantum dot (Chl-QD) was centrifuged briefly to remove large agglomerates of non-conjugated protein. Chl-QD was stored up to 1 week without significant aggregation. As shown in FIGS. 7A-7F, 8, and 9, the newly synthesized Chl-QD nanoparticles UV absorbance, size, charge, fluorescence and surface functional groups were characterized Example 4. Design of Chloroplast Targeting Peptide The chloroplast targeting sequence was designed from the Rubisco small subunit 1A (Genbank: OAP15425), having an amino acid sequence of SEQ ID NO: 2: MASSMLS-SATMVASPAQATMVAPFNGLKSSAAFPATRKANN-DITSITSNGGRVNCMQV WPPIGKKKFETL-SYLPDLTDSELAKEVDYLIRNKWIPCVEFDTDLCTV STVTHPDTMMDG TGQCGSFPCSVAPTPLK. The Chloroplast targeting sequence is highly conserved among dicot plants (FIG. 2A). Targeting sequence was truncated to first 12 amino acids to minimize the diameter of the functionalized quantum dot. The amino acid sequence contains one or more sequence motifs characterized by Lee et al., 2015, *Plant Physiology*, 169:471-484, the entire content of which is incorporated herein by reference, allowing import through the chloroplast double membrane (FIG. 1C). Sequence motifs found on the peptide allow for cytosolic recognition by chloroplast heat shock protein 70 (cpHsp70) and docking to translocation apparatus via translocon factor Toc159 (FIG. 1C). A short sequence containing GGC was added to the C-terminal end of the peptide as spacer. The terminal cysteine residue was utilized as conjugation site for SM-PEG linker onto the QD nanoparticles. Quantum dots functionalized with the chloroplast targeting sequence (Chl-QD) and MPA-capped QDs (MP-QD) were imaged by confocal microscopy as shown in FIGS. 2B-2D.

Example 5. Methyl Viologen and Ascorbic Acid Loading to Quantum Dots

Loading of methyl viologen and ascorbic acid into beta-cyclodextrin conjugated Chl-QD was carried out with some modification as described in in Saha et al., 2016, *Scientific Reports*, 6:35764 and Wang et al., 2013, *Carbon*, 59:192-199 the entire contents of both of which are incorporated herein by reference. In brief, methyl viologen or ascorbic acid were added in excess to a solution of 200 nM (0.017 mg/mL) Chl-QD. The mixture was vortexed and incubated for 0.5 h. The mixture was washed once through a 10,000 MW Column (Amicon® 10K) with double distilled water to remove excess molecules. Methyl viologen and ascorbic acid exhibit an absorbance (Abs) maximum at 260-265.5 nm. The inclusion complex concentration (MV-Chl-QD, and Asc-Chl-QD) was calculated based on the absorbance at 265.5 nm of reference to un loaded Chl-QD. The resultant MV-Chl-QD or Asc-Chl-QD concentration was extrapolated using a standard curve (FIGS. 7A-7F and 8).

Example 6. Quantum Dot Delivery into Leaves

All nanoparticles infiltrated into arabidopsis leaf lamina were dissolved in 10 mM TES buffer pH 7.0. The Chl-QD solution was diluted to 200 nM (0.17 mg/ml) and loaded with 60 µM methyl viologen or ascorbic acid. Nanoparticle solution was infiltrated into abaxial leaf lamina using a 1 ml needle syringe as described in in Wu et al., 2017, *Current Protocols in Chemical Biology*, 9:269-284, the entire content of which is incorporated herein by reference. To each plant, approximately 200 µl of solution was infiltrated into leaf mesophyll by gently pressing the tip of the syringe against the bottom of the leaf lamina and depressing the plunger. Excess solution was patted dry from the leaf surface.

Example 7. Preparation and Purification of Single Walled Carbon Nanotubes and DNA Complex Assembly The single walled carbon nanotubes (SWNT) surface was functionalized using positively charged amine polyethylenimine (PEI) molecules as outlined in FIG. 1B. SWCNTs were obtained from Sigma Aldrich and redispersed in 100 mL of deionized (DI) water, the pH of which was adjusted to 10 by using NaOH (20 mg/mL). The SWCNT solution was added slowly into 100 mL of PEI solution (2 mg/mL) while stirring. The mixture was stirred continuously for 0.5 hours before sealed in tubes and treated at 85° C. for 16 hours in the oven. After being cooled down to room temperature, the product was condensed and purified with molecular water by centrifugation at 4500 rpm (Allegra X30, Beckman) using Amicon® cell (MWCO 100K, Millipore Inc.) for 5 times. The final product (PEI-SWCNT) was collected and dispersed in 8 mL molecular water for future use. Coating SWCNT with PEI may be scaled up or down by keeping the SWCNT to PEI ratio as disclosed herein.

The synthesized PEI-SWCNTs (Sigma, pH 10.0) were purified by centrifugation at 16000 rcf, 90 min for at least 15 cycles, until no pellet was observed in the 1.5 mL Eppendorf tubes. The concentration of the purified PEI-SWCNT (Sigma, pH 10.0) was measured with UV-vis at 632 nm. The GFP DNA cassette was centrifuged at 16000 rcf, for 5 min to purify the DNA sample. The PEI-SWCNT was then mixed with GFP DNA cassette with 1:5 mass ratio. The optimal loading mass ratio between PEI-SWCNT and DNA cassette was checked by measuring the dynamic light scattering (DLS) size distribution with nanosizer instrument. After about 30 minutes, 10×TES buffer (100 mM, pH 7.1) was added to prepare the infiltrate solution (in 10 mM TES, pH 7.07) (FIGS. 11A-11D). The final PEI-SWCNT concentration was 10 mg/L.

Example 8. Preparation of the GFP Cassette Preparation

Figure 6B:
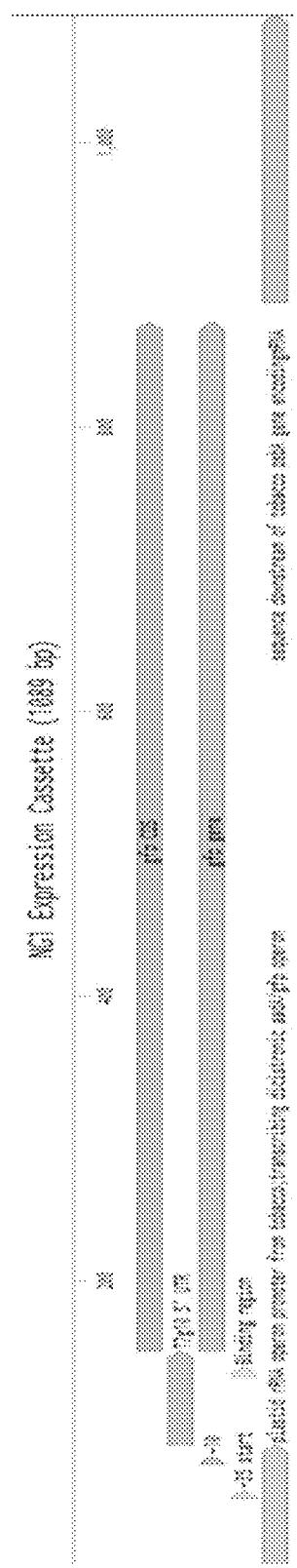
FIG. 6B is an annotated map of amplified GFP cassette bound to SWCNT (GFP-SWCNT), according to embodiments of the present disclosure.
Figure 7A:
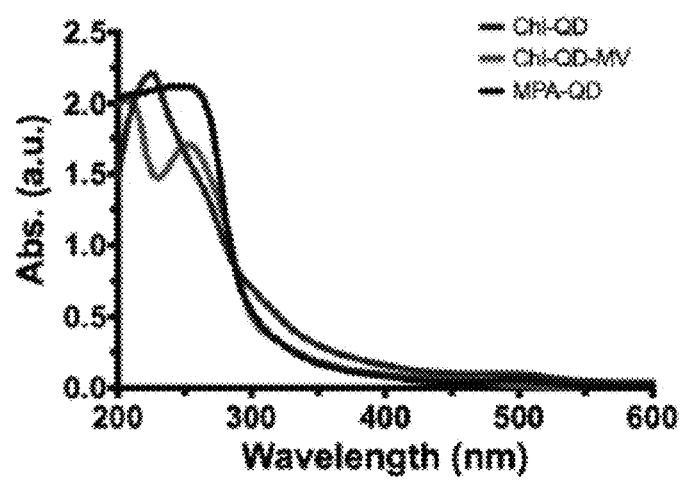
FIG. 7A shows the absorbance spectra measured by UV-vis spectrophotometer of MPA-QD, MV-Chl-QD, and Asc-Chl-QD, as indicated, according to embodiments of the present disclosure.
Figure 7B:
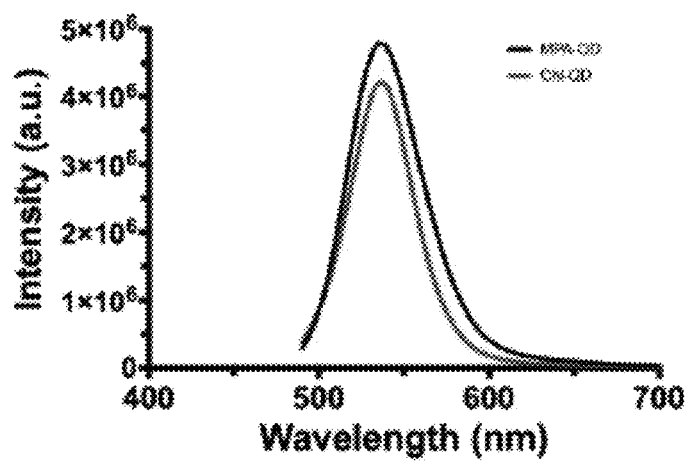
FIG. 7B shows the emission spectra measured by QM-400 spectrofluorometer for each of MPA-QD, MV-Chl-QD, and Asc-Chl-QD, as indicated, according to embodiments of the present disclosure.
Figure 7C:
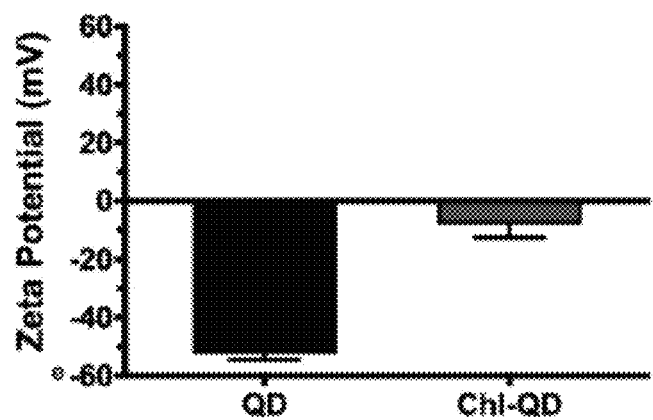
FIG. 7C is a graph of the Zeta potential for QD and Chl-QD, according to embodiments of the present disclosure.
Figure 7D:
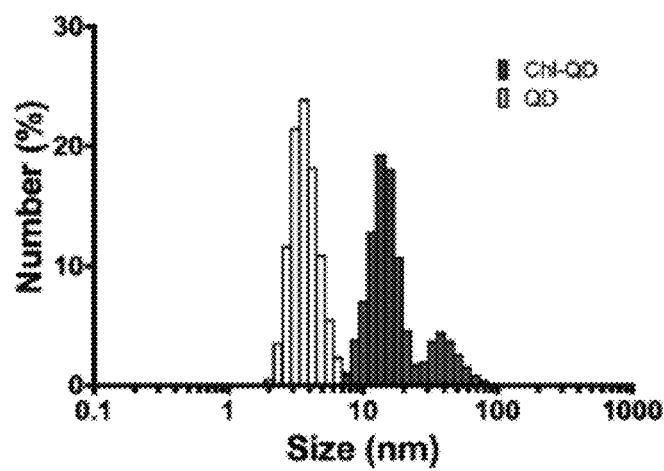
FIG. 7D is a graph of the hydrodynamic diameter of QD and Chl-QD (by dynamic light scattering DLS), according to embodiments of the present disclosure.
Figure 7E:
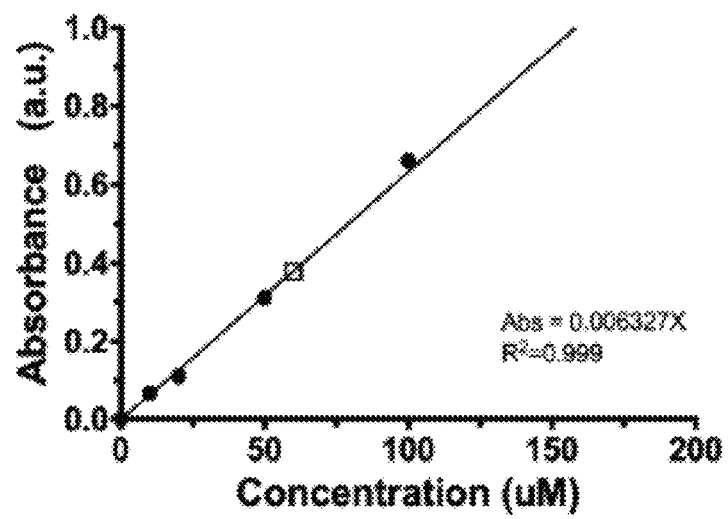
FIGS. 7E-7F are each graphs for the loading efficiency of MV and Asc in Chl-QD, as indicated, according to embodiments of the present disclosure.
Figure 7F:
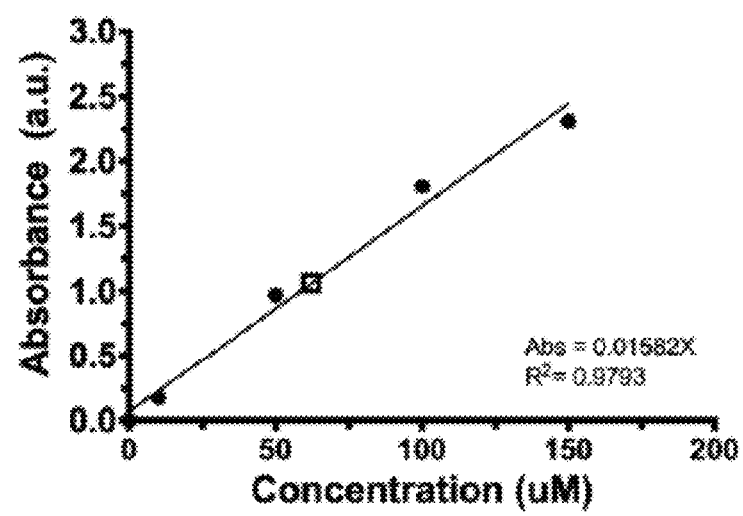
Figure 8:
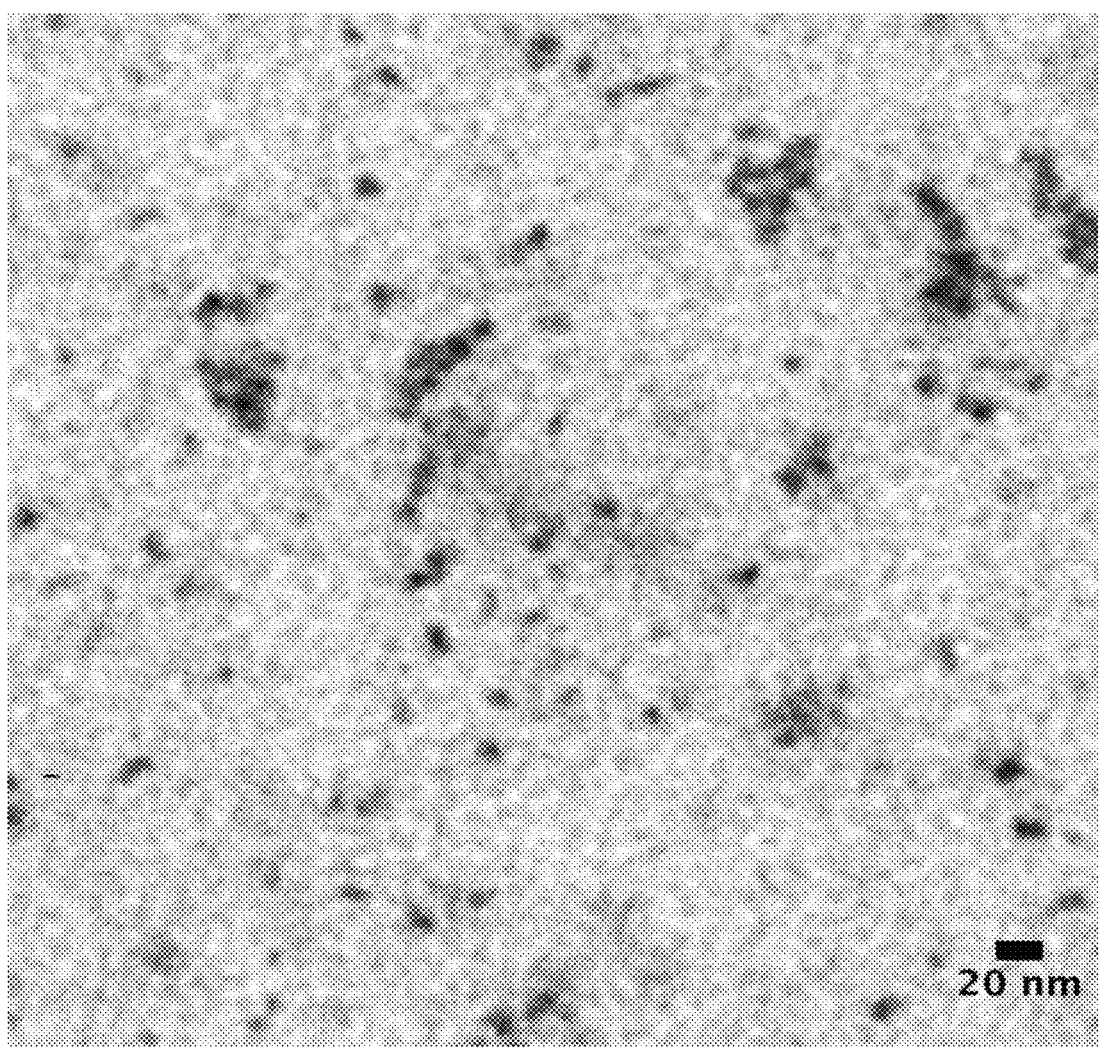
FIG. 8 is a transmission electron microscopy image of Chl-QDs showing an average diameter of 15.24±0.88 nm, according to embodiments of the present disclosure.

Plasmid Design. IDT Custom Gene Synthesis was used to synthesize the chloroplast protein expression cassette containing sequentially: 1) the chloroplast-specific promoter (Nt Prrn), 2) 5' UTR T7g10, commonly used with plastid rRNA operon (Prrn) for high total soluble proteins as described in Maliga and Bock, 2011, *Plant Physiology*, 155:1501-1510, the entire content of which is incorporated herein by reference, 3) GFP codon optimized for production within the chloroplast of *Arabidopsis thaliana* as described in Yu et al., 2017, *Plant Physiology*, 175:186-193, the entire content of which is incorporated herein by reference, and 4) the terminator region (Nt psbA) (FIGS. 6A-6C).

Figure 5A:
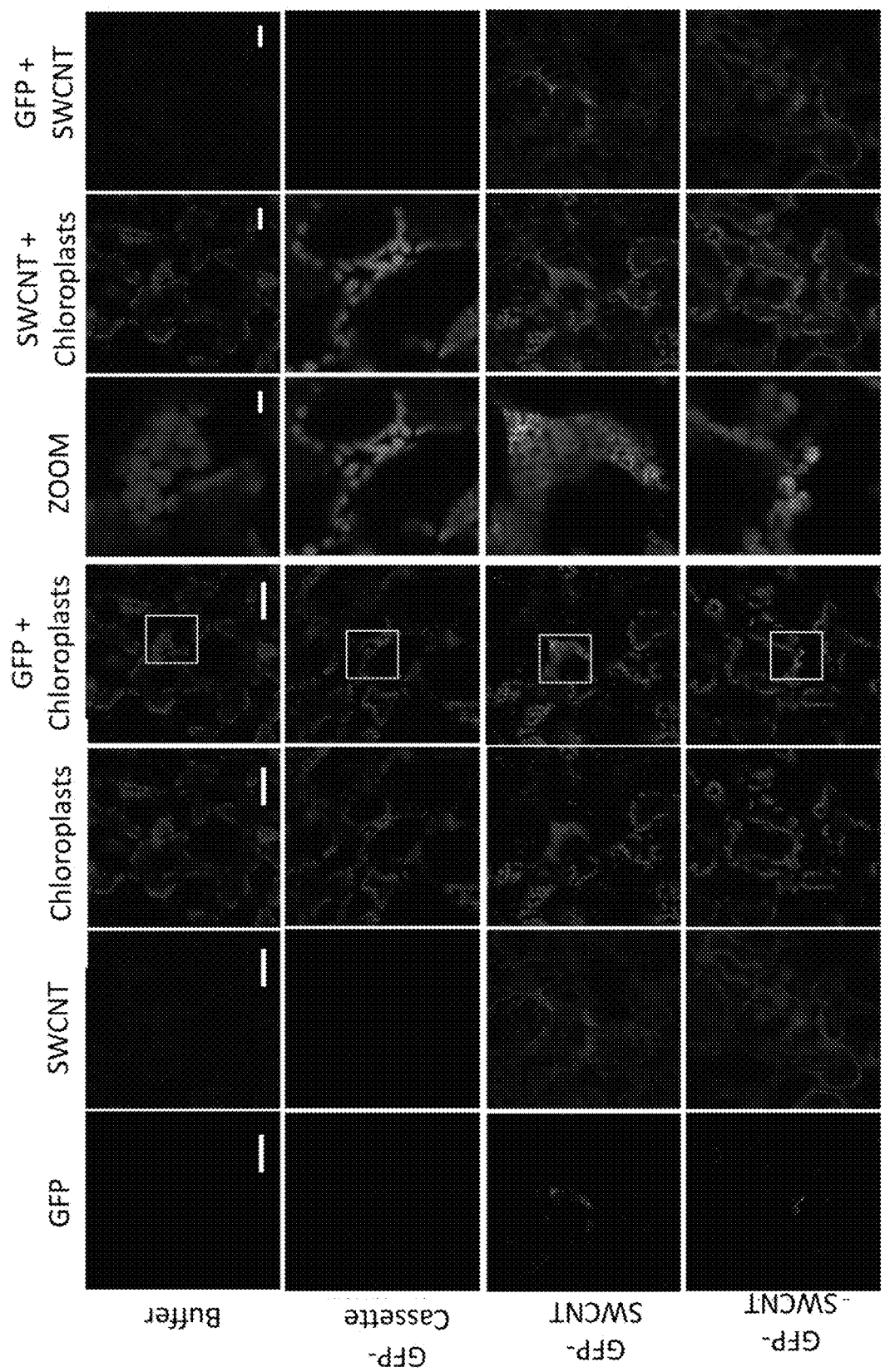
FIG. 5A shows confocal images of *Arabidopsis* leaf mesophyll cells showing SWNT distribution and GFP protein fluorescence signal in plants infiltrated by SWCNT coated with a GFP gene cassette (GFP-SWCNT) in which no GFP fluorescence was detected in leaf samples infiltrated with free GFP gene cassette or buffer, according to embodiments of the present disclosure, with a scale bar of 40 μm and zoom images at 10 μm.
Figure 5B:
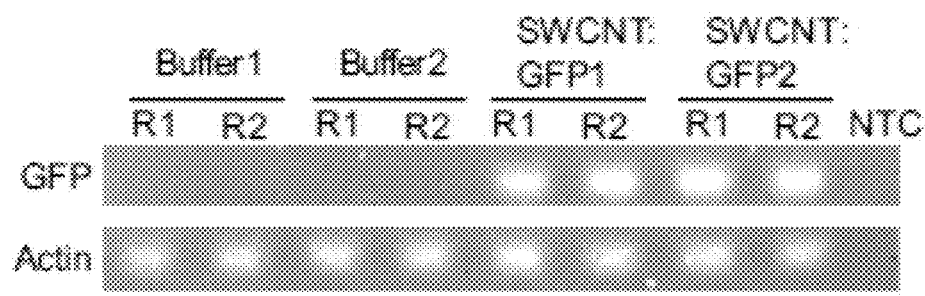
FIG. 5B is a semi-quantitative RT-PCR indicating the presence of GFP transcripts in plants infiltrated by GFP-SWCNT after 24 hours according to embodiments of the present disclosure.
Figure 5C:
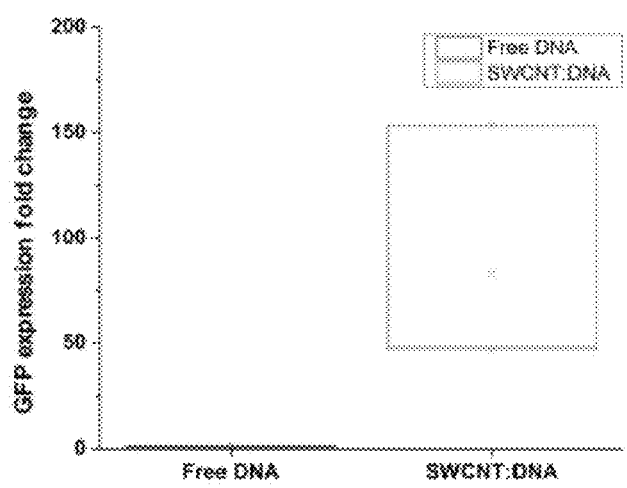
FIG. 5C is a graph comparing the quantitative RT-PCR analysis of GFP-SWCNT, Free GFP DNA, and buffer, according to embodiments of the present disclosure.
Figure 12:
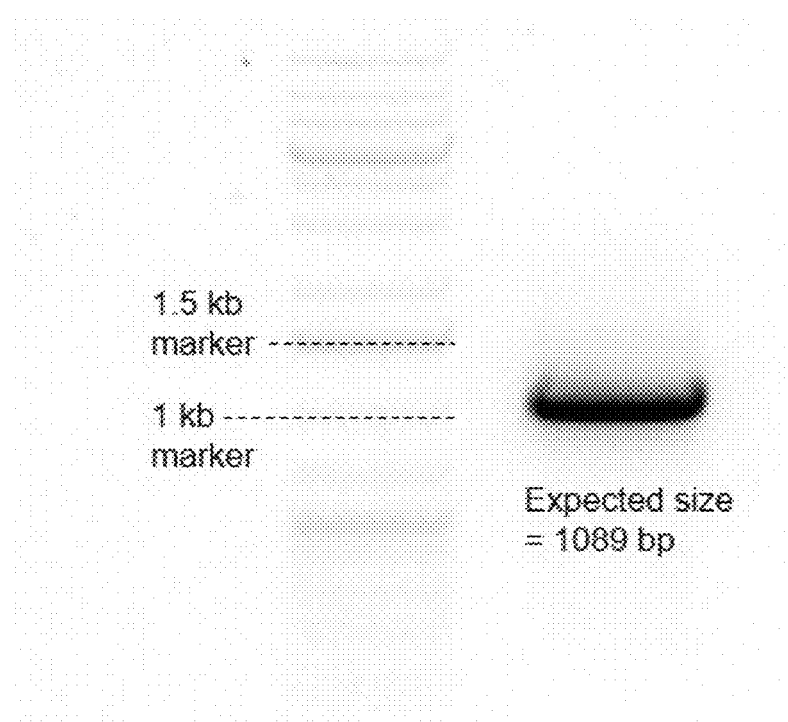
FIG. 12 is an image of a gel after electrophoresis of the GFP cassette complexed with SWCNT with confirmation of the correct band size after PCR and PCR purification for the chloroplast expression cassette in which the band shows a slightly larger size than the indicated 1 kb marker in the ladder, according to embodiments of the present disclosure.

Chloroplast Protein Expression Cassette Amplification. The chloroplast protein expression cassette (SEQ ID NO: 37) (FIG. 6C) driven by a chloroplast-specific promoter, was PCR amplified using PCR primers Nt-Prrn_F1: GCTCCCCCGCCGTCGTTCAAT (SEQ ID NO: 4); Nt-psbA_R1: AGCTTTGATCCCCCATGAATAAATGC (SEQ ID NO: 5) (Table 1) with OneTaq Hot Start (NEB, Cat #M0481S) and 2× Master Mix (NEB, Cat #M0482S). The PCR amplicon was purified (ThermoFisher, Cat #K0701) and confirmed by gel electrophoresis (FIG. 12).

er's instructions. With reference to FIGS. 5B-5C, RT-qPCR was performed using a Bio-Rad CFX Connect Real Time Thermal Cycler and SYBR green PCR reagent (Bio-Rad) as described in Vandesompele et al., 2002, *Genome Biology*, 3:research0034, the entire content of which is incorporated herein by reference, and the relative expression level of studied genes was analyzed by 2-ΔΔCT method as described in Livak and Schmittgen, 2011, Methods, 25:402-408, the entire content of which is incorporated herein by reference. Primers were designed to determine the GFP expression. The control gene (Actin and UBQ1) was used for normalization of the test gene transcript. Experiments were repeated in three individuals (each biological replicate was measured three times).

Example 8. Nanocomposition and Nanomaterial Measurements

Nanomaterial characterization. All nanomaterials were characterized for their concentration, size, charge, and fluorescence emission. Surface functional groups were analyzed using UV-vis absorbance, Dynamic light scattering (DLS), zeta potential, fluorescence emission spectra and FTIR analysis (FIGS. 7A-7F, 8, 9, 10, and 11A-11D).

Nanomaterial concentration. Absorbance measurements were carried out using a UV—2600 Shimadzu UV spectrophotometer. A quartz cuvette was filled with 1 ml of a 1:10 fold dilution of as-prepared nanoparticles. The concentration of the nanomaterials (mol/L) was determine using Lamberts—beer's law (Equation 1 and 2) to determine the extinction coefficient as described in Yu et al., 2003, *Chem-*

TABLE 1

| Genes | Primer sequences 5'-3' | Amplicon size (bp) |
|---|---|---|
| GFP | F: CTGTCAGTGGAGAGGGTGAAGG (SEQ ID NO: 6)<br>R: CCTGTTCCTTGGCCAACACTTG (SEQ ID NO: 7) | 99 |
| At-Actin | F: ACAACCGGTATTGTGCTGGA (SEQ II NO: 8)<br>R: CAAGACGGAGGATGGCATGA (SEQ ID NO: 9) | 94 |
| At-UBQI | F: CTTGTGTTGAGGCTTAGAGGAG (SEQ ID NO: 10)<br>R: CTTGGGTGAAGACGAGCATAG (SEQ ID NO: 11) | 113 |
| Nt-Prm_F1<br>Nt-psbA_R1 | F: GCTCCCCCGCCGTCGTTCAAT (SEQ ID NO: 4)<br>R: AGCTTTGATCCCCCATGAATAAATGC (SEQ ID NO: 5) | 1089 |

Carbon nanotube delivery into leaves. The GFP-SWCNT mixture was transferred into a 1 ml infiltration syringe and infiltrated into 4 week-old *Arabidopsis* plants. Buffer (10 mM TES buffer, pH 7.1) infiltrated plants were used as negative control. Free GFP DNA (in 10 mM TES buffer, pH 7.1) infiltrated plants were used as positive control. To avoid possible transferring of DNA-SWCNT from one leaf to another, different plants were used for buffer, free DNA, and also SWCNT-GFP. Kimwipes were used to remove the remaining solution to avoid contamination.

Gene expression and analysis. Four week-old *Arabidopsis* (Col-0) plant leaves infiltrated with buffer, free DNA GFP cassette, or DNA-SWCNT were excised, cut into small segments, and snap frozen in liquid nitrogen. The leaf RNA was extracted immediately by using Aurum TM Total RNA Mini Kit (Bio-Rad) following the manufacturer's instruction followed by a secondary DNase treatment to ensure no DNA cassette of GFP was carried over. The extracted RNA was then synthesized to cDNA by using iScript RT supermix (one-step cDNA mix, Bio-Rad) following the manufactur-

*istry of Materials*, 15:2854-2860, the entire content of which is incorporated herein by reference, where: Equation 1: $\epsilon=10043$ (Diameter), Equation 2: $Abs/\epsilon \times l$.

Dynamic light scattering (DLS) size and zeta potential. Zeta potential and sizes of nanomaterials were measured using a Malvern Zetasizer (Nano ZS) and sizer (Nano S) respectively. Sizes of as-prepared nanomaterials were used to extrapolate the extinction coefficient of equation 1 based on the diameter size.

Figure 9:
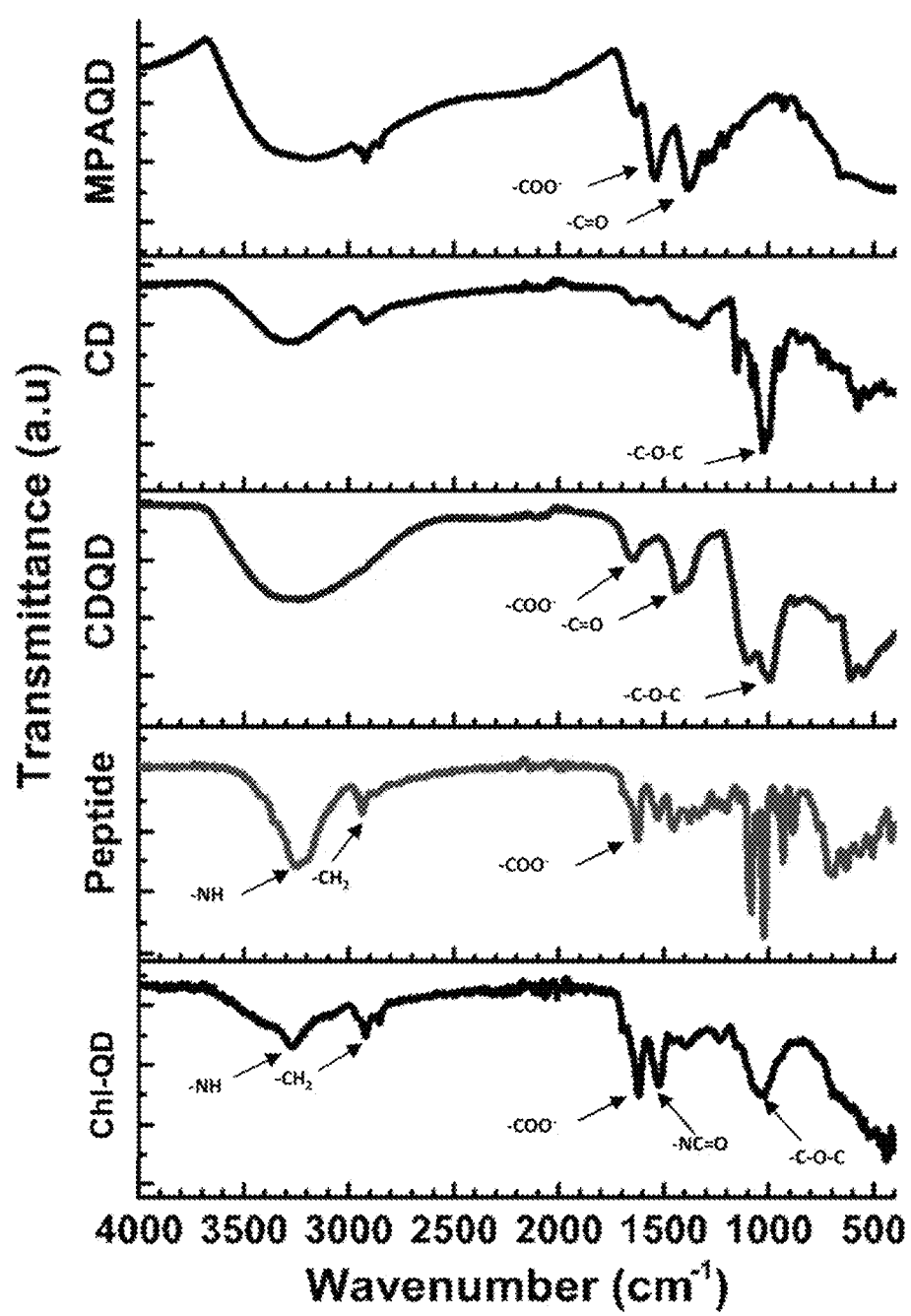
FIG. 9 shows graphs of Fourier-transform infrared (FTIR) spectra analysis of MPA-QD, cyclodextrin coated QD and Chl-QD, as indicated according to embodiments of the present disclosure.
Figure 10:
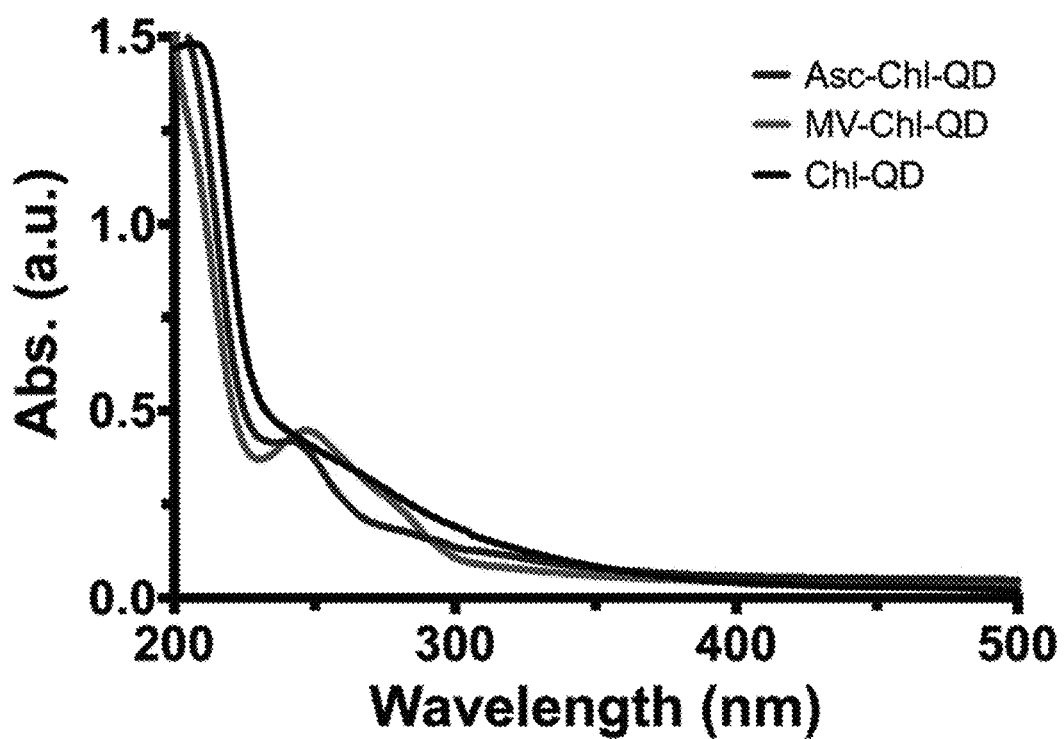
FIG. 10 is a graph of absorbance spectra of Chl-QD inclusion complexes with methyl viologen and ascorbic acid, MV-Chl-QD and Asc-Chl-QD respectively, according to embodiments of the present disclosure.
Figure 11A:
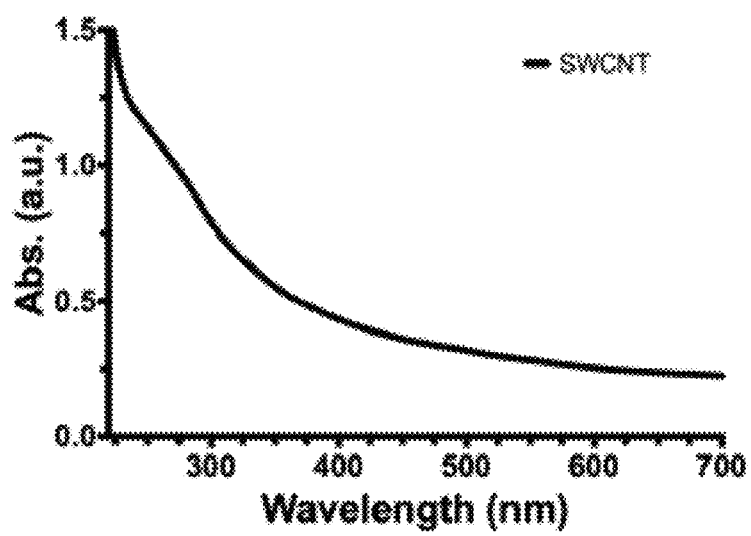
FIG. 11A is a graph of absorbance spectra of singe walled carbon nanotubes (SWCNT), as indicated, according to embodiments of the present disclosure.
Figure 11B:
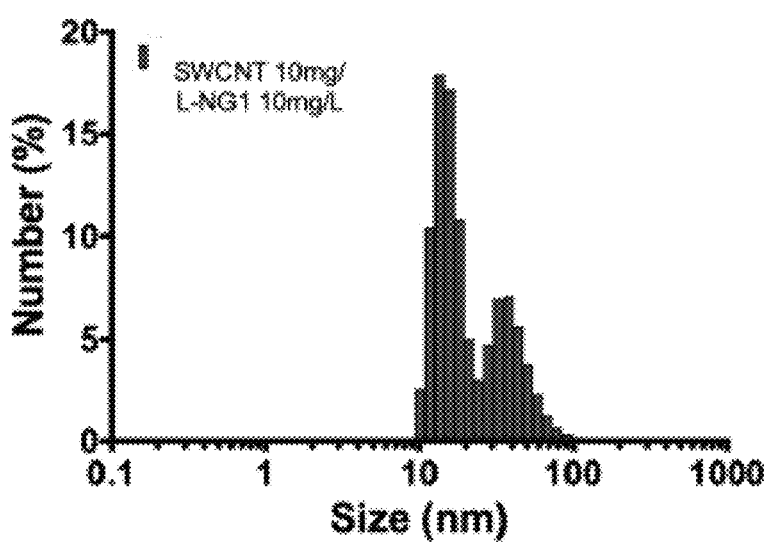
FIGS. 11B-11D are graphs representing the hydrodynamic diameter of SWCNT and GFP cassette complex ratios at 1:1, 1:5, and 1:10, as indicated, according to embodiments of the present disclosure.
Figure 11C:
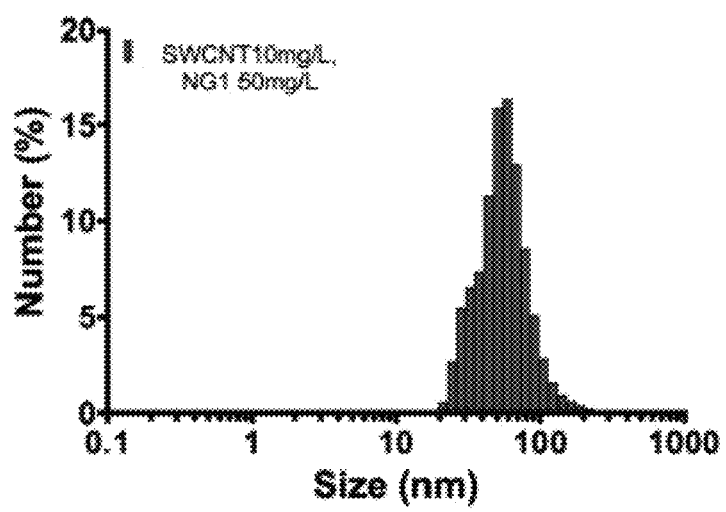
Figure 11D:
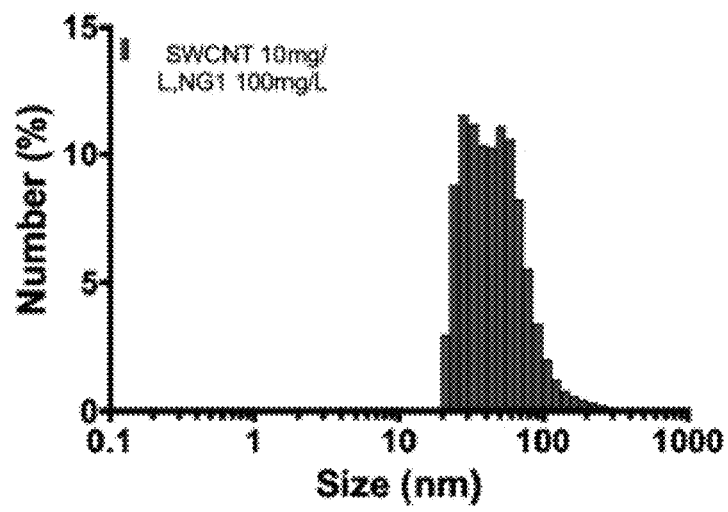

Fourier Transform Infrared Spectroscopy (FTIR). The surface coatings and functional groups on nanomaterials were characterized using Fourier transform infrared spectroscopy (FTIR) from Bruker (Alpha I). Samples from each step in synthesis of Chl-QD were taken to analyze functional groups on the nanoparticle surface (FIG. 9).

Transmission Electron Microscopy (TEM). TEM was performed on a Philips FEI Tecnai 12 microscope operated at an accelerating voltage of 120 kV. The TEM samples were prepared by placing one drop of particle solution (0.5 uM) onto the grid (400 mesh, Cu, Ted Pella) followed by drying naturally.

Confocal microscopy imaging of nanocompositions in leaves. *Arabidopsis* leaf samples were imaged by a Leica laser scanning confocal microscope TCS SP5 (Leica Microsystems, Germany). The imaging settings were as follows: 40× wet objective (Leica Microsystems, Germany); 405 nm laser excitation for Chl-QD; 514 nm for DHE; z-stack section thickness=2 nm; line average=4; PMT1, 500-550 nm for Chl-QD; 580-615 nm for DHE; PMT2, 720-780 nm for chloroplast autofluorescence. Three to eight individuals (4 leaf discs for each plant) in total were used. The z-stacks ("xyz") of two different regions were taken per leaf disc.

Example 9. In Vivo ROS Detection Assays

ROS detection assay was performed as described in in Owusu-Ansah and Banerjee, 2009, *Nature*, 461:537-541, Wu et al., 2017, *ACS Nano*, 11:11283-11297, the entire contents of both of which are incorporated herein by reference. Each leaf was infiltrated with 200 nM (0.017 mg/ml) Chl-QD, MV-Chl-QD or Asc-Chl-QD and incubated for assigned time. After incubation, a leaf punch was excised and incubated in 10 uM Dihydroethidium (Hydroethidine) (DHE) dye in 10 mM TES buffer at pH, 7.0 for 30 min. the leaf was immediately placed on a glass slide for confocal analysis.

Figure 3A:
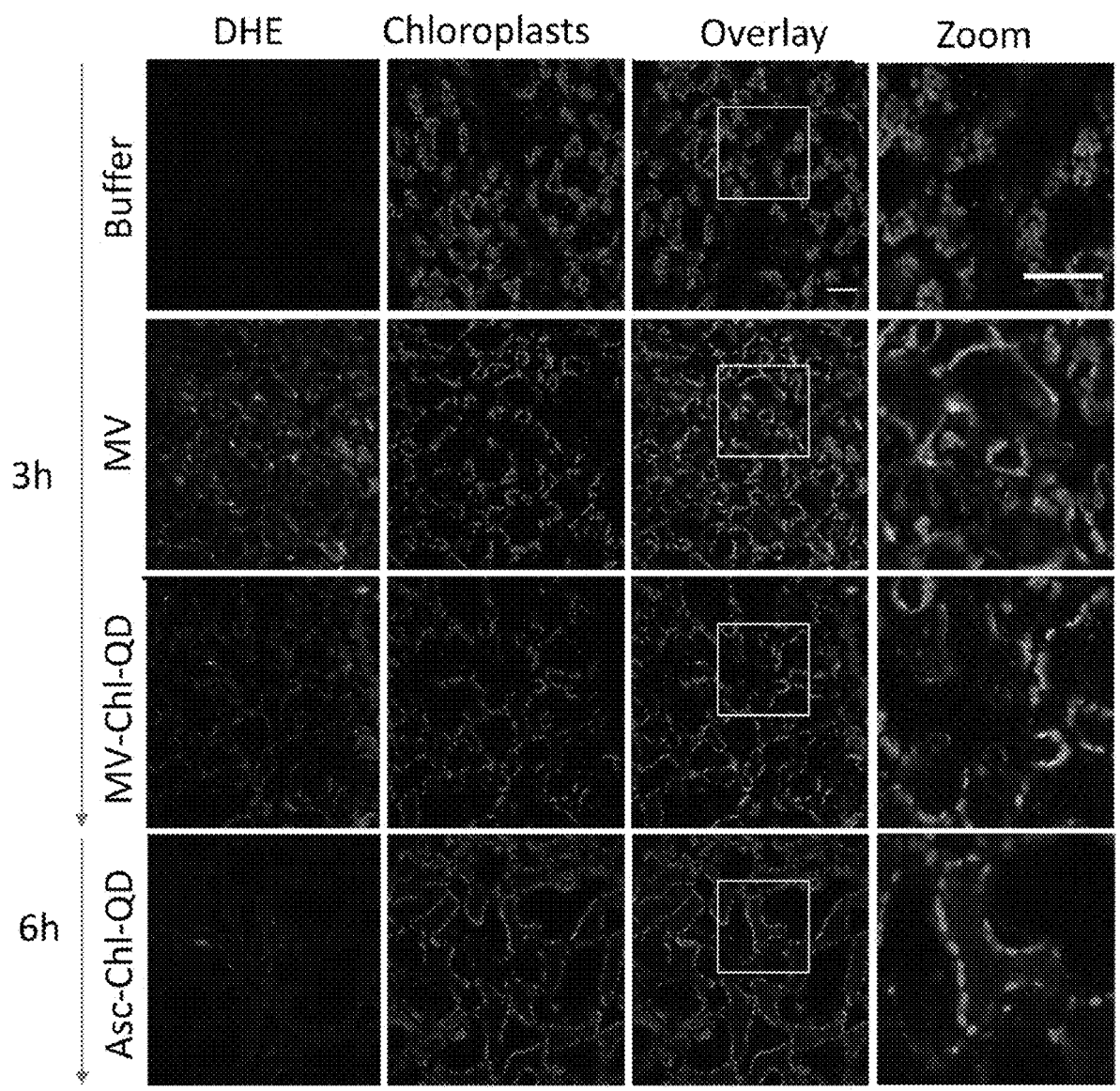
FIG. 3A shows confocal images of *Arabidopsis* leaf mesophyll cells illustrating the targeted generation and scavenging of superoxide anion (detected by DHE fluorescent dye) in chloroplasts by MV-Chl-QD and Asc-Chl-QD, respectively, according to embodiments of the present disclosure, with a scale bar of 40 μm.
Figure 3C:
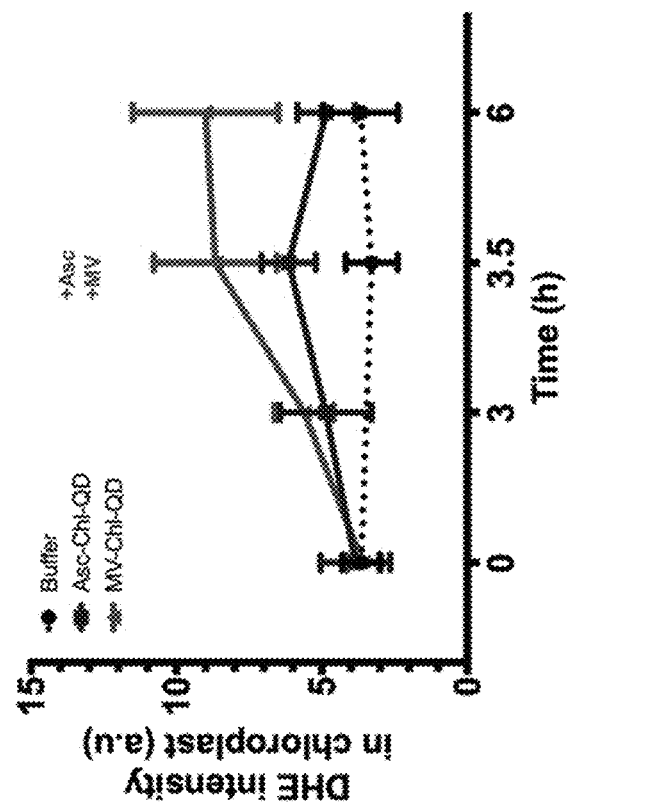
FIG. 3C is a graph of monitored DHE fluorescence signal intensity over time showing the subcellular increase and subsequent decrease of chloroplast ROS levels in plants infiltrated with 200 nM Chl-QD-MV loaded with 60 μM of methyl viologen at time 0 h; and the targeted decrease of superoxide anion generation in chloroplasts after delivery of 200 nM Asc-Chl-QD loaded with 60 μM of Ascorbic acid at time 3.5 hr (blue line), according to embodiments of the present disclosure, with the statistical analysis performed using one-way ANOVA with a Tukey post hoc test, and data expressed as mean±Standard deviation. (n=6-10). ***$P<0.001$, *$P<0.05$, and NS is not significant, according to embodiments of the present disclosure.
Figure 3B:
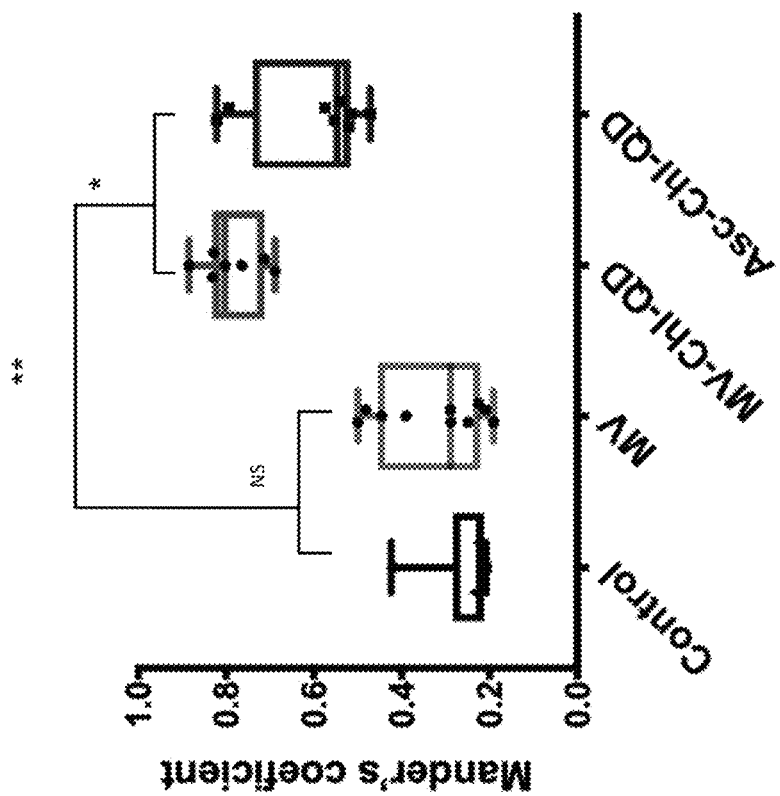
FIG. 3B is a graph of Mander's coefficient analysis showing a high level colocalization between chloroplasts and targeted ROS levels (detected by DHE fluorescent dye) in plants infiltrated with MV-Chl-QD or Asc-Chl-QD compared to methyl viologen alone, according to embodiments of the present disclosure.

DHE intensity and localization of MV/Asc-Chl-QD. With reference to FIGS. 3B-3C, the pixel intensity of DHE overlapping with chloroplast was quantified. The pixel intensity of DHE emission was measured with a region of interest (ROI) overlay mask of chloroplast distributed in each image.

Chloroplast and quantum dot colocalization. All confocal images were analyzed using FIJI (ImageJ). The corresponding distribution Chl-QD fluorescence and chloroplast autofluorescence profile intensities were measured across the six line sections of the ROI. The co-localization percentage of nanoceria in chloroplast was counted as the overlapped peaks of fluorescence emission of chloroplast pigments and Dil-labeled nanoceria.

With reference to at least FIGS. 1A-1B, 2B, 3A, and 5A, the functionalized quantum dot targeted to the chloroplast of plants and the functionalized single walled carbon nanotubes (SWNT) complexed with DNA cassettes for plastid-specific transcription allow for a broad range of applications from improving the understanding of plant biology, enhancing crop yields, to transforming plants into technology by delivering genes to chloroplasts encoding high value proteins.

While the present disclosure has been illustrated and described with reference to certain exemplary embodiments, those of ordinary skill in the art will understand that various modifications and changes may be made to the described embodiments without departing from the spirit and scope of the present disclosure, as defined in the following claims.

What is claimed is:

1. A composition of a nanoparticle linked to a chloroplast-targeting peptide, the composition comprising:
   the nanoparticle; and
   a conjugation linker comprising a first end moiety conjugated to the nanoparticle, a second end moiety conjugated to the chloroplast-targeting peptide, and a molecular basket comprising cyclodextrin and positioned between the first end moiety and the second end moiety;
   wherein the chloroplast-targeting peptide comprises a chloroplast-targeting sequence of the ribulose bisphosphate carboxylase small chain 1A (RBCS1A) protein that consists of SEQ ID NO:1.

2. The composition of claim 1, wherein each of the first end moiety and the second end moiety of the conjugation linker are independently selected from a group comprising a carboxyl, an amine, a thiol, a maleimide, a hydroxyl, a hydrazide, an azide, a biotin, or a succinimidyl ester (NHS ester).

3. The composition of claim 1, wherein the composition further comprises a molecule that forms an inclusion complex with the cyclodextrin.

4. The composition of claim 3, wherein the molecule that forms an inclusion complex with the cyclodextrin is selected from the group consisting of allyl isothiocyanate, chlorpyrifos, hesperetin, hesperidin, naringenin, naringin, 2-methyl-5-(1-methylethyl) (carvacrol), nicotinic acid, ascorbic acid, methyl viologen, dihydroxyphenylalanine (L-DOPA), theophylline, amatadine, beta-carotene, nitrophenol isomers, alkaline phosphatase, naphthalene, terfenadine, carvedilol, sulindac, fenoprofen, albendazole, and cocaine.

5. The composition of claim 4, wherein the molecule that forms an inclusion complex with the cyclodextrin is ascorbic acid or methyl viologen.

6. The composition of claim 1, wherein a three amino acid spacer of X1-X2-Cysteine (C) is added to the end of the targeting sequence, where X1 and X2 are each any amino acid and the Cysteine (C) is conjugated to the second end moiety of the conjugation linker.

7. The composition of claim 6, wherein X1 and X2 are each independently selected from glycine or histidine.

8. The composition of claim 7, wherein the three amino acid spacer is glycine-glycine-cysteine.

9. The composition of claim 1, wherein the first end moiety of the conjugation linker comprises a mercaptocarboxylic acid selected from the group consisting of mercaptoacetic acid, mercaptopropionic acid, mercaptosuccinic acid, mercaptobenzoic acid, mercaptoundecanoic acid, and combinations thereof.

10. The composition of claim 1, wherein the second end moiety comprises sulfosuccinimidyl 4-[N-maleimidomethyl] cyclohexane-1-carboxylate (Sulfo-SMCC), succinimidyl-([N-maleimidopropionamido]-n-ethyleneglycol) ester $(SM(PEG)_n)$ with n=2, 4, 6, 8, 12, or 24, and/or 1-Ethyl-3-[3-dimethylaminopropyl]carbodiimide hydrochloride-N hydroxysulfosuccinimide (EDC-Sulfo-NHS).

11. The composition of claim 1, wherein the nanoparticle is a quantum dot.

12. A method of transporting a molecule to a chloroplast of a plant, the method comprising:
    administering the composition of claim 3 to a leaf of the plant.

13. The method of claim 12, wherein the plant is a dicot plant.

14. The composition of claim 8, wherein the chloroplast-targeting peptide consists of SEQ ID NO: 3.

15. The composition of claim 1, wherein the nanoparticle is a quantum dot having a core comprising carbon, nitrogen, oxygen, or any combination of carbon, nitrogen, and oxygen.

16. The composition of claim 1, wherein the nanoparticle is a quantum dot having a core comprising cadmium telluride (CdTe), cadmium selenide (CdSe), $CdSe_xTe_{1-x}$, cadmium sulfide (CdS), indium arsenide (InAs), indium lead (InPb), cadmium lead sulfide (plumbanethione-cadmium) (CdPbS), zinc tin sulfide (ZnSnS), zinc sulfide (ZnS), lead sulfide (PbS), lead selenide (Pb Se), lead telluride (PbTe), mercury sulfide (HgS), mercury selenide (HgSe), mercury telluride (HgTe), cadmium mercury telluride (CdHgTe), gallium arsenide (GaAs), or an alloy thereof.

* * * * *

SEQUENCE LISTING

```
<160> NUMBER OF SEQ ID NOS: 37

<210> SEQ ID NO 1
<211> LENGTH: 12
<212> TYPE: PRT
<213> ORGANISM: Arabidopsis thaliana

<400> SEQUENCE: 1

Met Ala Ser Ser Met Leu Ser Ser Ala Thr Met Val
1               5                   10

<210> SEQ ID NO 2
<211> LENGTH: 135
<212> TYPE: PRT
<213> ORGANISM: Arabidopsis thaliana

<400> SEQUENCE: 2

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
                20                  25                  30

Phe Pro Ala Thr Arg Lys Ala Asn Asn Asp Ile Thr Ser Ile Thr Ser
            35                  40                  45

Asn Gly Gly Arg Val Asn Cys Met Gln Val Trp Pro Pro Ile Gly Lys
        50                  55                  60

Lys Lys Phe Glu Thr Leu Ser Tyr Leu Pro Asp Leu Thr Asp Ser Glu
65                  70                  75                  80

Leu Ala Lys Glu Val Asp Tyr Leu Ile Arg Asn Lys Trp Ile Pro Cys
                85                  90                  95

Val Glu Phe Asp Thr Asp Leu Cys Thr Val Ser Thr Val Thr His Pro
                100                 105                 110

Asp Thr Met Met Asp Gly Thr Gly Gln Cys Gly Ser Phe Pro Cys Ser
            115                 120                 125
```

-continued

Val Ala Pro Thr Pro Leu Lys
    130             135

<210> SEQ ID NO 3
<211> LENGTH: 15
<212> TYPE: PRT
<213> ORGANISM: Artificial Sequence
<220> FEATURE:
<223> OTHER INFORMATION: Rubisco 1A targeting with spacer

<400> SEQUENCE: 3

Met Ala Ser Ser Met Leu Ser Ser Ala Thr Met Val Gly Gly Cys
1               5                   10                  15

<210> SEQ ID NO 4
<211> LENGTH: 21
<212> TYPE: DNA
<213> ORGANISM: Artificial Sequence
<220> FEATURE:
<223> OTHER INFORMATION: Nt-Prrn F1 primer

<400> SEQUENCE: 4 gctccccgc cgtcgttcaa t                                          21

<210> SEQ ID NO 5
<211> LENGTH: 26
<212> TYPE: DNA
<213> ORGANISM: Artificial Sequence
<220> FEATURE:
<223> OTHER INFORMATION: Nt-psbA R1

<400> SEQUENCE: 5
agctttgatc ccccatgaat aaatgc                                    26

<210> SEQ ID NO 6
<211> LENGTH: 22
<212> TYPE: DNA
<213> ORGANISM: Artificial Sequence
<220> FEATURE:
<223> OTHER INFORMATION: GFP F primer

<400> SEQUENCE: 6
ctgtcagtgg agagggtgaa gg                                        22

<210> SEQ ID NO 7
<211> LENGTH: 22
<212> TYPE: DNA
<213> ORGANISM: Artificial Sequence
<220> FEATURE:
<223> OTHER INFORMATION: GFP R primer

<400> SEQUENCE: 7
cctgttcctt ggccaacact tg                                        22

<210> SEQ ID NO 8
<211> LENGTH: 25
<212> TYPE: DNA
<213> ORGANISM: Artificial Sequence
<220> FEATURE:
<223> OTHER INFORMATION: AtGAPDH-A F primer

<400> SEQUENCE: 8
tggttgatct cgttgtgcag gtctc                                     25

<210> SEQ ID NO 9
<211> LENGTH: 24

<212> TYPE: DNA
<213> ORGANISM: Artificial Sequence
<220> FEATURE:
<223> OTHER INFORMATION: AtGAPDH-A R primer

<400> SEQUENCE: 9
gtcagccaag tcaacaactc tctg    24

<210> SEQ ID NO 10
<211> LENGTH: 20
<212> TYPE: DNA
<213> ORGANISM: Artificial Sequence
<220> FEATURE:
<223> OTHER INFORMATION: At-Actin F primer

<400> SEQUENCE: 10
acaaccggta ttgtgctgga    20

<210> SEQ ID NO 11
<211> LENGTH: 20
<212> TYPE: DNA
<213> ORGANISM: Artificial Sequence
<220> FEATURE:
<223> OTHER INFORMATION: At-Actin R primer

<400> SEQUENCE: 11
caagacggag gatggcatga    20

<210> SEQ ID NO 12
<211> LENGTH: 22
<212> TYPE: DNA
<213> ORGANISM: Artificial Sequence
<220> FEATURE:
<223> OTHER INFORMATION: At-UBQ1 F primer

<400> SEQUENCE: 12
gcgtcttcgt ggtggtttct aa    22

<210> SEQ ID NO 13
<211> LENGTH: 25
<212> TYPE: DNA
<213> ORGANISM: Artificial Sequence
<220> FEATURE:
<223> OTHER INFORMATION: At-UBQ R primer

<400> SEQUENCE: 13
gaaagagata acaggaacgg aaaca    25

<210> SEQ ID NO 14
<211> LENGTH: 30
<212> TYPE: PRT
<213> ORGANISM: Brassica napus

<400> SEQUENCE: 14

Met Ala Ser Ser Met Leu Ser Ser Ala Thr Val Val Ser Ser Pro Ala
1               5                   10                  15

Gln Ala Ala Met Val Ala Pro Phe Thr Gly Leu Lys Ser Ser
            20                  25                  30

<210> SEQ ID NO 15
<211> LENGTH: 30
<212> TYPE: PRT
<213> ORGANISM: Brassica juncea

<400> SEQUENCE: 15

Met Ala Ser Ser Met Leu Ser Ser Ala Ala Val Val Thr Ser Pro Ala
1               5                   10                  15

Gln Ala Thr Met Val Ala Pro Phe Thr Gly Leu Lys Ser Ser
            20                  25                  30

<210> SEQ ID NO 16
<211> LENGTH: 30
<212> TYPE: PRT
<213> ORGANISM: Brassica rapa

<400> SEQUENCE: 16

Met Ala Ser Ser Met Leu Ser Ser Ala Ala Val Val Thr Ser Pro Ala
1               5                   10                  15

Gln Ala Thr Met Val Ala Pro Phe Thr Gly Leu Lys Ser Ser
            20                  25                  30

<210> SEQ ID NO 17
<211> LENGTH: 36
<212> TYPE: PRT
<213> ORGANISM: Prunus persica

<400> SEQUENCE: 17

Met Ala Ser Ser Met Ile Ser Ser Ala Thr Val Ala Ser Val Tyr Ala
1               5                   10                  15

Asp Arg Ala Ala Pro Ala Gln Ala Ser Leu Val Ala Pro Phe Thr Gly
            20                  25                  30

Leu Lys Ser Ala
            35

<210> SEQ ID NO 18
<211> LENGTH: 36
<212> TYPE: PRT
<213> ORGANISM: Prunus avium

<400> SEQUENCE: 18

Met Ala Ser Ser Met Ile Ser Ser Ala Thr Val Ala Ser Val Tyr Ala
1               5                   10                  15

Asp Arg Ala Ala Pro Ala Gln Ala Ser Leu Val Ala Pro Phe Thr Gly
            20                  25                  30

Leu Lys Ser Ala
            35

<210> SEQ ID NO 19
<211> LENGTH: 31
<212> TYPE: PRT
<213> ORGANISM: Gossypium hirsutum

<400> SEQUENCE: 19

Met Ala Ser Ser Met Ile Ser Ser Ala Thr Ile Ala Thr Ala Ser Pro
1               5                   10                  15

Ala Gln Ala Asn Met Val Ala Pro Phe Thr Gly Leu Lys Ser Ala
            20                  25                  30

<210> SEQ ID NO 20
<211> LENGTH: 34
<212> TYPE: PRT
<213> ORGANISM: Vitis vinifera

<400> SEQUENCE: 20

Met Ala Ser Ser Met Val Ser Ser Ala Thr Val Ala Thr Ile Asn Arg
1               5                   10                  15

Ala Thr Pro Ala Gln Ala Asn Met Val Ala Pro Phe Thr Gly Leu Lys
            20                  25                  30

Ser Leu

<210> SEQ ID NO 21
<211> LENGTH: 34
<212> TYPE: PRT
<213> ORGANISM: Ricinus communis

<400> SEQUENCE: 21

Met Ala Ser Ser Met Leu Ser Thr Ala Thr Val Ala Ser Leu Asn Arg
1               5                   10                  15

Ala Ser Pro Ala Gln Ala Ser Met Val Ala Pro Phe Thr Gly Leu Lys
            20                  25                  30

Ser Thr

<210> SEQ ID NO 22
<211> LENGTH: 34
<212> TYPE: PRT
<213> ORGANISM: Camellia sinensis

<400> SEQUENCE: 22

Met Ala Ser Ser Met Ile Ser Ser Thr Thr Val Ala Thr Ala Asn Arg
1               5                   10                  15

Ala Ser Leu Ala Gln Ala Ser Met Val Ala Pro Phe Thr Gly Leu Lys
            20                  25                  30

Ser Ser

<210> SEQ ID NO 23
<211> LENGTH: 34
<212> TYPE: PRT
<213> ORGANISM: Medicago truncatula

<400> SEQUENCE: 23

Met Ala Ser Ser Met Ile Ser Ser Ala Met Thr Thr Val Asn Arg
1               5                   10                  15

Ala Ser Ser Val Gln Ser Gly Ala Val Ala Pro Phe Val Gly Leu Lys
            20                  25                  30

Ser Met

<210> SEQ ID NO 24
<211> LENGTH: 34
<212> TYPE: PRT
<213> ORGANISM: Cicer arietinum

<400> SEQUENCE: 24

Met Ala Ser Ser Met Ile Ser Ser Ala Ala Val Thr Thr Val Asn Arg
1               5                   10                  15

Ala Ser Ser Val Gln Ser Gly Ala Val Ala Pro Phe Val Gly Leu Lys
            20                  25                  30

Ser Met

<210> SEQ ID NO 25
<211> LENGTH: 34
<212> TYPE: PRT
<213> ORGANISM: Coffea arabica

<400> SEQUENCE: 25

Met Ala Ser Ser Met Ile Ser Ser Ala Ala Val Ala Thr Thr Thr Arg
1               5                   10                  15

Ala Ser Pro Ala Gln Ala Ser Met Val Ala Pro Phe Asn Gly Leu Lys
            20                  25                  30

Ala Ala

<210> SEQ ID NO 26
<211> LENGTH: 34
<212> TYPE: PRT
<213> ORGANISM: Hevea brasiliensis

<400> SEQUENCE: 26

Met Ala Ser Ser Met Leu Ser Thr Ala Ala Val Ala Cys Ile Asn Arg
1               5                   10                  15

Ala Ser Pro Ala Gln Ala Ser Met Val Ala Pro Phe Thr Gly Leu Lys
            20                  25                  30

Ser Thr

<210> SEQ ID NO 27
<211> LENGTH: 32
<212> TYPE: PRT
<213> ORGANISM: Nicotiana attenuata

<400> SEQUENCE: 27

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

<210> SEQ ID NO 28
<211> LENGTH: 33
<212> TYPE: PRT
<213> ORGANISM: Solanum tuberosum

<400> SEQUENCE: 28

Met Ala Ser Ser Val Ile Ser Ser Ala Ala Val Ala Thr Arg Thr Asn
1               5                   10                  15

Val Thr Gln Ala Ser Ser Met Val Ala Pro Phe Thr Gly Leu Lys Ser
            20                  25                  30

Thr

<210> SEQ ID NO 29
<211> LENGTH: 32
<212> TYPE: PRT
<213> ORGANISM: Solanum lycopersicum

<400> SEQUENCE: 29

Met Ala Ser Ser Val Ile Ser Ser Ala Ala Val Ala Thr Arg Ser Asn
1               5                   10                  15

Val Thr Gln Ala Ser Met Val Ala Pro Phe Thr Gly Leu Lys Ser Ser
            20                  25                  30

<210> SEQ ID NO 30
<211> LENGTH: 33
<212> TYPE: PRT
<213> ORGANISM: Proteus vulgaris

<400> SEQUENCE: 30

Met Ala Ser Ser Met Ile Ser Ser Pro Ala Val Thr Thr Val Asn Arg
1               5                   10                  15

Ala Gly Ala Gly Ala Gly Met Val Ala Pro Phe Thr Gly Leu Lys Ser
            20                  25                  30

Leu

<210> SEQ ID NO 31
<211> LENGTH: 31
<212> TYPE: PRT
<213> ORGANISM: Glycine max

<400> SEQUENCE: 31

```
Met Ala Ser Ser Met Ile Ser Ser Pro Ala Val Thr Thr Val Asn Arg
1               5                   10                  15

Ala Gly Ala Gly Met Val Ala Pro Phe Thr Gly Leu Lys Ser Met
            20                  25                  30
```

<210> SEQ ID NO 32
<211> LENGTH: 32
<212> TYPE: PRT
<213> ORGANISM: Capsicum annuum

<400> SEQUENCE: 32

```
Met Ala Ser Ser Val Met Ser Ile Ala Thr Val Ala Thr Gly Ala Asn
1               5                   10                  15

Ala Ala Gln Ala Ser Met Ile Ala Ser Phe Asn Gly Leu Lys Ser Ala
            20                  25                  30
```

<210> SEQ ID NO 33
<211> LENGTH: 32
<212> TYPE: PRT
<213> ORGANISM: Vigna radiata

<400> SEQUENCE: 33

```
Met Ala Ser Ser Met Ile Ser Ser Pro Ala Val Thr Thr Val Asn Arg
1               5                   10                  15

Ala Gly Ala Ala Gly Met Val Ala Pro Phe Thr Gly Leu Lys Ser Leu
            20                  25                  30
```

<210> SEQ ID NO 34
<211> LENGTH: 33
<212> TYPE: PRT
<213> ORGANISM: Musa acuminata

<400> SEQUENCE: 34

```
Met Ala Ser Ser Met Met Val Ser Ser Ala Ala Thr Val Ser Arg Ala
1               5                   10                  15

Ser Pro Ala Gln Ser Ser Met Val Ala Pro Phe Thr Gly Leu Lys Ser
            20                  25                  30

Thr
```

<210> SEQ ID NO 35
<211> LENGTH: 34
<212> TYPE: PRT
<213> ORGANISM: Arachis hypogaea

<400> SEQUENCE: 35

```
Met Ala Ile Ser Met Ile Ser Ser Pro Ala Val Thr Thr Val Ser Arg
1               5                   10                  15

Ala Ser Pro Ala Gln Ala Asn Met Val Ala Pro Phe Thr Gly Leu Lys
            20                  25                  30

Ser Leu
```

<210> SEQ ID NO 36

```
<211> LENGTH: 30
<212> TYPE: PRT
<213> ORGANISM: Arabidopsis thaliana

<400> SEQUENCE: 36

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser
                20                  25                  30

<210> SEQ ID NO 37
<211> LENGTH: 1089
<212> TYPE: DNA
<213> ORGANISM: Artificial Sequence
<220> FEATURE:
<223> OTHER INFORMATION: pUCIDT-KAN_g10-AtGFP sequence

<400> SEQUENCE: 37
gctcccccgc cgtcgttcaa tgagaatgga taagaggctc gtgggattga cgtgaggggg        60
cagggatggc tatatttctg ggaggggaga ccacaacggt ttcccactag aaataatttt       120
gtttaacttt aagaaggaga tatacatatg atggctagca gtaaaggaga agaacttttc       180
actggagttg tcccaattct tgttgaatta gatggtgatg ttaatgggca caaattttct       240
gtcagtggag agggtgaagg tgatgcaaca tacggaaaac ttacccttaa atttatttgc       300
actactggaa aactacctgt tccttggcca acacttgtca ctactttctc ttatggtgtt       360
caatgctttt caagataccc agatcatatg aagcggcacg acttcttcaa gagcgccatg       420
cctgagggat acgtgcagga gaggaccatc tctttcaagg acgacgggaa ctacaagaca       480
cgtgctgaag tcaagtttga gggagacacc ctcgtcaaca ggatcgagct taagggaatc       540
gatttcaagg aggacggaaa catcctcggc cacaagttgg aatacaacta caactcccac       600
aacgtataca tcacggcaga caacaaaag aatggaatca agctaacttt caaaattaga       660
cacaacattg aagatggaag cgttcaacta gcagaccatt atcaacaaaa tactccaatt       720
ggcgatggcc ctgtcctttt accagacaac cattacctgt ccacacaatc tgccctttcg       780
aaagatccca acgaaaagag agaccacatg gtccttcttg agtttgtaac agctgctggg       840
attacacatg gcatggatga actatacaaa taagctctag ctagagcgat cctggcctag       900
tctataggag gttttgaaaa gaaggagca ataatcattt tcttgttcta tcaagagggt       960
gctattgctc ctttctttt ttcttttat ttatttacta gtattttact tacatagact      1020 ttttgttta cattatagaa aaagaaggag aggttatttt cttgcattta ttcatggggg      1080
atcaaagct                                                              1089
```